US012709717B2

(12) United States Patent
Merten et al.

(10) Patent No.: US 12,709,717 B2
(45) **Date of Patent: *Aug. 18, 2026**

(54) CANDLE AND METHOD OF MAKING THEREOF

(71) Applicant: S. C. JOHNSON & SON, INC., Racine, WI (US)

(72) Inventors: Anthony Merten, Racine, WI (US); Victoria Martinez, Racine, WI (US)

(73) Assignee: S. C. JOHNSON & SON, INC., Racine, WI (US)

( * ) Notice: Subject to any disclaimer, the term of this patent is extended or adjusted under 35 U.S.C. 154(b) by 364 days.

This patent is subject to a terminal disclaimer.

(21) Appl. No.: 18/213,706

(22) Filed: Jun. 23, 2023

(65) Prior Publication Data

US 2023/0416639 A1 Dec. 28, 2023

Related U.S. Application Data

(60) Provisional application No. 63/355,820, filed on Jun. 27, 2022.

(51) Int. Cl.

| | |
|---|---|
| ***C11C 5/02*** | (2006.01) |
| ***A01M 1/20*** | (2006.01) |
| ***A01M 29/12*** | (2011.01) |
| ***A61L 9/03*** | (2006.01) |
| ***F23D 3/16*** | (2006.01) |

(52) U.S. Cl.

CPC ............ *C11C 5/02* (2013.01); *A01M 1/2066* (2013.01); *A01M 29/12* (2013.01); *A61L 9/037* (2013.01); *F23D 3/16* (2013.01)

(58) Field of Classification Search

CPC ...... A61L 9/037; A61L 9/127; A01M 1/2044; A01M 1/2077; A01M 1/2088; A01M 1/2066; A01M 29/12

See application file for complete search history.

(56) References Cited

U.S. PATENT DOCUMENTS

| | | |
|---|---|---|
| 4,323,193 A | 4/1982 | Compton et al. |
| 5,840,257 A | 11/1998 | Bureau et al. |

(Continued)

FOREIGN PATENT DOCUMENTS

| | | |
|---|---|---|
| CN | 204369843 U | 6/2015 |
| WO | 2016028152 A1 | 2/2016 |

(Continued)

OTHER PUBLICATIONS

Glade, Exotic Tropical Blossoms® 3-Wick Candle, Retrieved from https://glade.com/en-us/products/candles/3-wick/exotic-tropical-blossoms, Copyright 2025 S.C. Johnson & Son, Inc., Version Accessed on Jun. 30, 2025, 5 pages.

(Continued)

*Primary Examiner* — Ko-Wei Lin

(74) *Attorney, Agent, or Firm* — Quarles & Brady LLP

(57) ABSTRACT

The present disclosure provides a volatile material dispensing device that includes a container, a wax composition, a wick, and a sleeve having or formed at least in part by a volatile material, for example, a fragrance or pest control material. The sleeve is positioned between the wax composition and the container and configured to be exposed and release volatile material as the wax composition is consumed by the wick via combustion.

20 Claims, 15 Drawing Sheets

(56) References Cited

U.S. PATENT DOCUMENTS 6,152,728 A 11/2000 Griffel
6,210,153 B1 * 4/2001 Freeman ................. F21S 13/12 431/126
7,637,738 B2 12/2009 Conover
7,837,355 B2 11/2010 Schnuckle
8,070,319 B2 12/2011 Schnuckle et al.
8,132,936 B2 3/2012 Patton et al.
8,342,712 B2 1/2013 Patton et al.
8,534,869 B2 9/2013 Patton et al.
8,550,660 B2 10/2013 Patton et al.
8,646,946 B2 2/2014 Schnuckle et al.
8,695,891 B2 4/2014 Santini et al.
8,696,166 B2 4/2014 Patton et al.
8,721,118 B2 5/2014 Patton et al.
8,727,569 B2 5/2014 Schnuckle et al.
9,080,762 B2 7/2015 Ray
9,393,335 B2 7/2016 Santini et al.
9,643,204 B2 5/2017 Ray
10,018,313 B2 7/2018 Schnuckle et al.
10,472,526 B2 11/2019 Sarkis et al.
10,502,377 B2 12/2019 Schnuckle et al.
10,533,719 B2 1/2020 Schnuckle et al.
10,533,721 B2 1/2020 Schnuckle et al.
10,774,289 B2 9/2020 Lombardo et al.
10,976,020 B2 4/2021 Schnuckle et al.
10,989,381 B2 4/2021 Schnuckle et al.
11,105,481 B2 8/2021 Schnuckle et al.
2002/0114904 A1 8/2002 Chang
2011/0294081 A1 * 12/2011 McLaren ................ C11C 5/008 431/291
2012/0135359 A1 * 5/2012 Thomas .................... F23D 3/40 431/291
2012/0270164 A1 * 10/2012 Dickmann ................ C11C 5/02 431/291
2015/0342172 A1 * 12/2015 Sharma ................. A01M 29/12 431/291
2017/0275476 A1 9/2017 Sarkis et al.
2021/0227864 A1 7/2021 Blandino et al.
2021/0401726 A1 * 12/2021 Miller ..................... C11C 5/002
2022/0057058 A1 2/2022 Schnuckle et al.

FOREIGN PATENT DOCUMENTS

WO 2019197824 A2 10/2019
WO 2019236614 A1 12/2019
WO 2020171609 A1 8/2020
WO 2021216965 A1 10/2021
WO 2024006209 A1 4/2024

OTHER PUBLICATIONS

Glade, Orchid & Neroli 3-Wick Candle, Retrieved from Orchid & Neroli 3-Wick Candle, Copyright 2025 S.C. Johnson & Son, Inc., Version Accessed on Jun. 30, 2025, 4 pages.

PCT International Search Report and Written Opinion, PCT/US2023/026229, Dec. 6, 2023, 20 pages.

International Search Report and Written Opinion from corresponding Application No. PCT/US2025/042670 mailed Dec. 5, 2025, 19 pages.

* cited by examiner

700

CANDLE AND METHOD OF MAKING THEREOF

CROSS-REFERENCE TO RELATED APPLICATIONS

This application is related to, claims priority benefit of, and incorporates herein by reference for all purposes U.S. Provisional Patent Application 63/355,820, filed on Jun. 27, 2022.

BACKGROUND OF THE INVENTION

Candles made from paraffin or other types of wax are well known and processes used to manufacture candles can vary. However, candles, and the process of producing candles, is an art that continues to see improvements. In their simplest form, candles are composed of a wax or paraffin composition with a fragrance and a wick extending therethrough. Further, a user may ignite the wick, which burns the wick, melts the wax, and emits the fragrance in the wax composition. However, in addition to emitting a fragrance, candles can produce and emit soot and other emissions in the form of volatile organic compounds (VOCs) when the candle burns, which is undesirable.

SUMMARY OF THE INVENTION

In one aspect, the present disclosure provides a volatile material dispensing device that includes a container, a wax composition, a wick, and a sleeve having a volatile material. Further, according to this aspect, the sleeve is positioned between the wax composition and the container.

In further embodiments, the volatile material dispensing device includes a wax composition that is essentially free of a fragrance. The sleeve may also be constructed from a permeable material capable of passive emanation of the volatile material. Further, in some embodiments, the wax composition and the container enclose the sleeve and the volatile material. In these embodiments, the volatile material dispensing device may also further include a strip with the volatile material and the strip may be positioned above the wax composition. In other embodiments, a portion of the sleeve extends above the wax composition and is exposed. Further, the volatile material may be selected from the group consisting of a fragrance or a pest control agent, and the volatile material dispensing device may be a candle. In further embodiments, the volatile material dispensing device may include three wicks. In other embodiments, the sleeve may be positioned at least partially between the wax and the container, and the sleeve may include three reservoirs positioned radially outward from the wicks. More so, in some embodiments, the sleeve is constructed from a material selected from the group consisting of a polyethylene (PE), a polyvinyl alcohol (PVOH), a polypropylene (PP), an ethylene-vinyl acetate (EVA), a high-density polyethylene (HDPE), an ethylene vinyl alcohol (EVOH), or a blend thereof.

According to another aspect, the present disclosure provides a volatile material dispensing device that includes a container having a permeable interior surface, a non-permeable exterior surface, and a volatile material between or within the permeable interior surface and the non-permeable exterior surface. In this embodiment, the volatile material dispensing device further includes a wax composition and a wick.

In further embodiments, the wax composition is essentially free of a fragrance and the non-permeable exterior wall includes a sealant layer. In other embodiments, the volatile material is selected from the group consisting of a fragrance or a pest control agent and the volatile dispensing device may be a candle. Additionally, in some embodiments, a portion of the permeable interior surface of the container is exposed and the container is constructed from a material that includes at least one of terracotta and concrete. Here, the candle may also include three wicks.

In other embodiments, the present disclosure provides a candle that includes a wick, a wax composition essentially free of a fragrance, and a container that includes a volatile material.

According to other aspects of the present disclosure, a method of making a candle is provided. According to one embodiment, the method includes the steps of providing a container and a reservoir having a volatile material, positioning the reservoir adjacent an interior surface of the container, positioning a wick in the container, pouring a wax composition in the container, and allowing the wax composition to solidify. According to another embodiment, the method includes the steps of providing a container having a volatile material, positioning a wick in the container, pouring a wax composition in the container, and allowing the wax composition to solidify.

The foregoing and other aspects and advantages of the disclosure will appear from the following description. In the description, reference is made to the accompanying drawings, which form a part hereof, and in which there is shown by way of illustration a preferred configuration of the disclosure. Such configuration does not necessarily represent the full scope of the disclosure, however, and reference is made therefore to the claims herein for interpreting the scope of the disclosure.

BRIEF DESCRIPTION OF THE DRAWINGS

The invention will be better understood and features, aspects, and advantages other than those set forth above will become apparent when consideration is given to the following detailed description thereof. Such detailed description makes reference to the following drawings.

Figure 1:
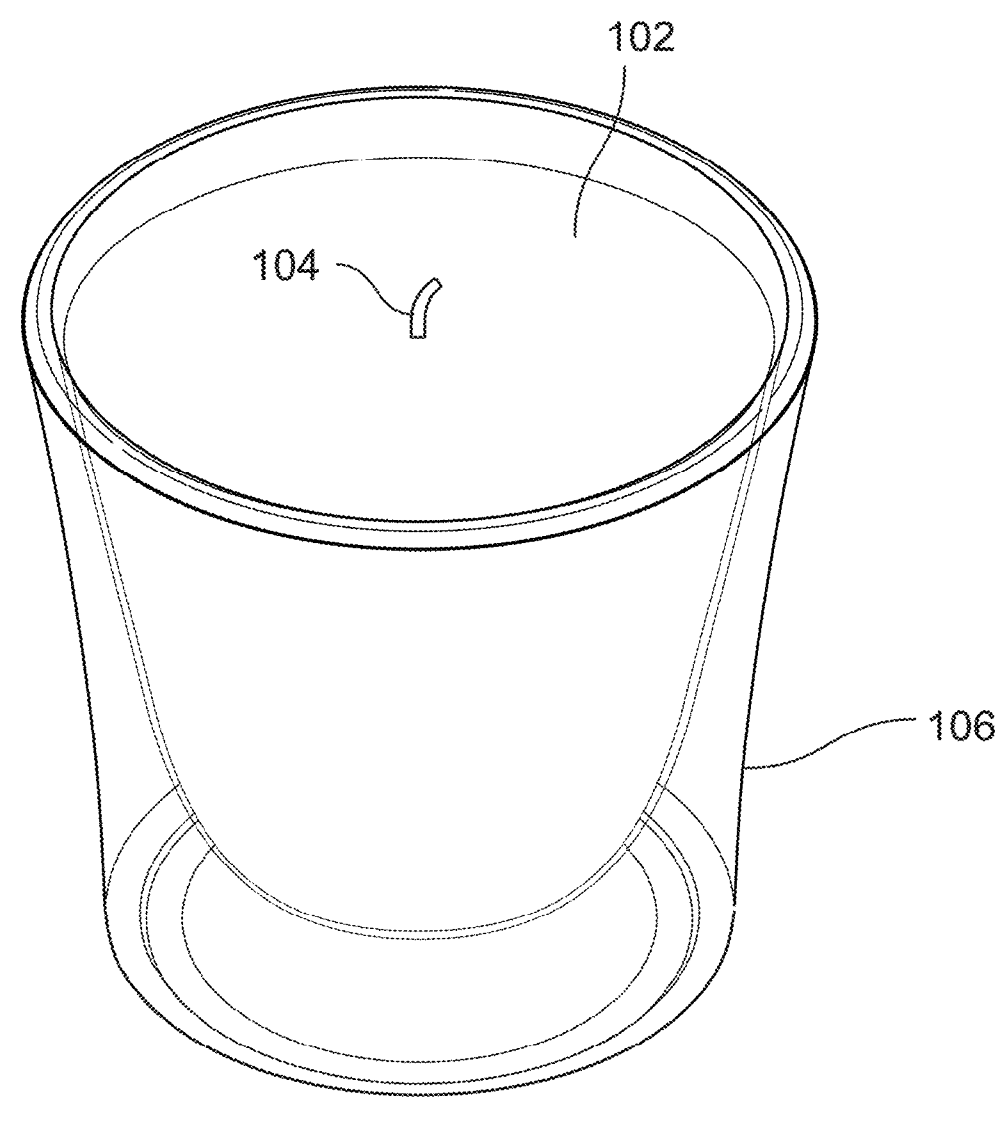
FIG. 1 is a perspective view of a candle of the prior art.

Before the embodiments of the disclosure are explained in detail, it is to be understood that the disclosure is not limited in its application to the details of construction and the arrangement of the components set forth in the following description or illustrated in the drawings. The disclosure is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures. The figures, which are not necessarily to scale, depict selected embodiments and are not intended to limit the scope of embodiments of the invention. Skilled artisans may also recognize that the examples provided herein have many useful alternatives and fall within the scope of embodiments of the invention.

Referring to the figures generally, an improved candle capable of providing a cleaner, more complete fragrance delivery is depicted. The candles of the present disclosure, unlike typical candles of the prior art, include a wax or fuel composition devoid, substantially free of, or essentially free of a fragrance, volatile material, or active agent. Rather, the candles of the present disclosure include the fragrance, volatile material, or active agent in another element of the candle. In one embodiment, as shown in FIGS. 2-9, a sleeve or reservoir having a fragrance, volatile material, or active agent is positioned between the wax or fuel composition and an interior wall or surface of a candle jar, vessel, or container. According to another aspect of the present disclosure, which is shown in FIGS. 10-18, the fragrance, volatile material, or active agent is positioned in the candle jar, vessel, or container and at least a portion of an interior wall or surface of the candle jar, vessel, or container is permeable, such that the fragrance, volatile material, or active agent emanates or passes through the interior wall of the container when the wax or fuel composition melts or burns.

Typical candles of the prior art include a wax composition having a fragrance mixed therein, a wick extending through the wax composition, and a jar or vessel that holds the wax composition. Therefore, when a user lights the wick, the wax melts, and a pool of molten wax forms, which allows for evaporation of the fragrance. However, the fragrance in the wax is also burned as the wax is heated and burned, which sometimes causes the formation and emission of soot or particulates, and the emission of volatile organic compounds (VOCs), such as benzene or naphthalene, into the ambient or surrounding environment. This formation and emission of particulates and VOCs by the candle occurs, at least in part, because of an incomplete combustion of the melted wax in the flame of the candle.

The candles or volatile material dispensers of the present disclosure, however, include a wax or fuel composition essentially free of, substantially free of, or devoid of a fragrance or active agent (e.g., a pest control agent). Rather than placing the fragrance, volatile material, or active agent in the wax composition, the candles of the present disclosure include the fragrance, volatile material, or active agent in another element of the candle. In one embodiment, for example, the candle includes a sleeve or reservoir with the fragrance, volatile material, or active agent. In this embodiment, the sleeve or reservoir strip is positioned between the wax or fuel composition and ajar or container that holds the wax or fuel composition. Therefore, as the wax or fuel composition burns and melts, it exposes the sleeve or reservoir to the ambient or surrounding environment, which allows emanation of the fragrance, volatile material, or active agent with substantially less particulates and VOC emissions.

In another embodiment, the jar or container of the candle itself includes the fragrance, volatile material, or active agent and the jar or container emanates the fragrance, volatile material, or active agent as the candle burns. For example, in one embodiment, at least a portion of an interior wall of the candle jar or vessel is porous or permeable and an exterior wall of the candle jar or vessel is sealed, non-porous, or non-permeable. Therefore, as the candle burns and the wax or fuel composition melts, an increased surface area of the interior wall of the candle jar or vessel is exposed, which allows for emanation of the fragrance or volatile material from the candle. This may be referred to as the hot throw of the candle.

The candles of the present disclosure produce less particulates and less VOC emissions compared to a traditional candle because the fragrance, volatile material, and/or active agent is positioned away from the wick and flame of the candle. In addition to lowering particulate and VOC emissions, the candles of the present disclosure provide a more desirable fragrance, as the fragrance, volatile material, or active agent will not have a smoky character, for example. Thus, the smell and delivery of the fragrance, volatile material, and/or active agent is cleaner and stronger than a traditional candle.

Still further, the candles of the present disclosure are more efficient and more cost effective than traditional candles. In particular, about half of a fragrance or volatile material of a traditional candle is never even experienced by a user when a typical candle is burned because half of the fragrance is burned as it travels up the wick and into the flame of the candle and by being proximate the flame of the candle. The candles of the present disclosure, however, overcome this issue by placing the fragrance, volatile material, and/or active agent away from the wax composition, the wick, and the flame of the candle. As a result, the fragrance, volatile material, or active agent of the present disclosure are not burnt in the flame of the candle or fragrance device. Thus, in addition to lowering particulate and VOC emissions, the candles of the present disclosure can also use less fragrance and cost less without sacrificing the user experience.

Additionally, a further advantage of the candle of the present disclosure is the relative ease in which the candle can be manufactured and can be manufactured with minimal impact on current production processes and supply chains. As will be described herein, the fragranced or dosed sleeves or reservoir strips can be produced on separate off-line processes and then can be easily added to the manufacturing process, thereby having minimal impact on the current production process and supply chain. Similarly, the vessels or containers having a fragrance or volatile material therein may be produced on separate off-line processes and then inserted into the manufacturing process with minimal impact on the current production process and supply chain.

Even further, as the wax or fuel composition no longer includes a fragrance, volatile material, or active agent, the wax or fuel composition can be consistent across manufacturing lines or product lines. For example, a candle having a first fragrance may include a wax composition identical to a wax composition of a second candle having a second fragrance that is different than the first fragrance. This is advantageous for several reasons. First, the commonality and uniformity between the wax or fuel composition between products and product lines allows for the use of the same wick across products and product lines, which allows for more efficient production lines and material cost savings. Previously, for example, a first wick may be more effective at wicking a first wax composition with a first fragrance and a second wick may be more effective at wicking a second wax composition with a second fragrance; therefore, two different wicks would have to be produced or purchased and inserted into the product lines. This complexity is not present with the candles of the present disclosure because the fragrance, volatile material, or active agent is present in a portion of the candle other than the wax or fuel composition and the wax or fuel composition is devoid, essentially free of, or substantially free of a fragrance, volatile material, or active agent. Thus, a single fuel or wax composition can be used across candles or dispensers with varying fragrances, volatile materials, or active agents, and as a result, a single wick can also be used across candles or dispensers without affecting the emanation of the fragrances, volatile materials, or active agents. This also provides a more reliable candle because a candle does not need to be tested each time a new wax composition with a new fragrance is launched. Typically, several different wick sizes and materials are tested to determine the best performing wick when a new fragrance is introduced. This testing aims to ensure the wick, fragrance, and wax composition performs within a set of criteria for temperature, carbon emissions, blooms, soot emission, and curvature of the wick during use. This testing and optimization are not required for the candles of the present disclosure. Rather, an optimal wick need only be developed once and this optimal wick can be subsequently used, regardless of changes in the fragrance, volatile material, or active agent.

Further, some fragrances, active agents, or volatile materials are also incompatible or insoluble with some wax or fuel compositions. As a result, some fragrances, active agents, or volatile materials cannot be used in traditional candles. The candles or dispensers of the present disclosure, however, overcome this issue because the fragrance, active agent, or volatile material is present in a portion of the candle other than the wax or fuel composition. The candles and dispensers of the present disclosure therefore allow the use of some fragrances, active agents, or volatile materials that were previously incompatible with traditional candles.

Additionally, although this disclosure is primarily focused on fragranced candles, the candles of the present disclosure, and the method of producing the candles, can be used for other chemical ingredients and volatile materials. For example, the embodiments of this disclosure and the method described herein could be a solution for pest control products. With that said, some fragrance materials, pest control actives, and other volatile materials may be less soluble or insoluble in wax compositions. Alternatively, or additionally, some fragrances, pest control actives, and other volatile materials may suppress or inhibit a candle flame, thereby producing a less desirable flame to a user when they are present in the wax composition. Further, some fragrances, volatile materials, or active agents are insoluble or incompatible with wax compositions. The candles of the present disclosure are also advantageous because the placement of the fragrance or volatile material in a permeable sleeve eliminates or greatly reduces these negative effects or drawbacks of standard candles. More particularly, the permeable sleeve or reservoir strip, or the vessel or container, can be constructed from a material that is compatible with a broader range of chemistries or can be customized to work best with various chemistries based on the solubility and chemical characteristics of the fragrance, volatile material, or active agent to be employed in the candle or fragrance device.

Definitions

As used herein, the term "essentially free of" or "substantially free of" may mean that the indicated material (e.g., a fragrance, volatile material, or active agent) is present in an amount of no more than 0.1 wt. % by weight of a composition (e.g., fuel composition or wax composition), or preferably not present at an analytically detectible level in such compositions. It may also include compositions where the indicated material is present only as an impurity of one or more of the materials deliberately added to such compositions.

As used herein, the term "fragrance" is meant as including any perfume or aroma ingredient or a mixture thereof. A "fragrance" is meant here as a compound which is of current use in the perfumery or aroma industry, i.e., a compound which is used as an active ingredient in perfumed or aroma candles in order to impart a hedonic effect into its ambient or surrounding environment. Put differently, a "fragrance" is an ingredient or mixture that imparts or modifies a surrounding environment with a positive or pleasant odor. More so, this definition is also meant to include compounds that do not necessarily have an odor, but are capable of modulating the odor of a perfuming composition and, as a result, of modifying the perception by a user of the odor of such a composition. In general, these fragrance ingredients belong to chemical classes as varied as alcohols, aldehydes, ketones, esters, ethers, acetates, nitriles, terpene, hydrocarbons, nitrogenous or sulphureous heterocyclic compounds and essential oils, and said perfuming ingredients can be of natural or synthetic origin.

Further, the term "volatile material" used herein encompasses fragrances, as well as any other compounds that emanate or evaporate to provide an effect at normal ambient temperatures (e.g., 15-23° C.) or elevated temperatures produced by a candle flame. For example, a "volatile material" may be a fragrance that imparts a surrounding environment with a positive or pleasant odor, a pest control agent that acts to repel insects (e.g., mosquitos), or any other compound that emanates to provide an effect to the surrounding environment. Further, "volatile material" may refer to a chemical composition having an active agent, as well as other ingredients. For example, the term "volatile material" may refer to a composition having an active agent—such as a fragrance, an insecticide, a deodorizer, a fungicide, a bacteriocide, a sanitizer, a pet barrier, or other active volatile compound—and a carrier liquid or solvent—such as an oil-based, organic based, and/or water based carrier or solvent, a deodorizing liquid, or the like, and/or combinations thereof. In particular embodiments, the "volatile material" may include an insect control agent, an insect repellant, or an insecticide. Examples of possible insecticides that may be suitable in the "volatile material" include pyrethroids such as metafluthrin, transfluthrin, tefluthrin, and vaporthrin, or natural actives (geraniol, etc.) or a blend of these insecticides. Additional examples of an active agent that may be used in the "volatile material" may include RAID®, Pyrel®, POLIL®, AUTAN®, OUST™ or GLADE®, sold by S. C. Johnson & Son, Inc., of Racine, Wisconsin. The "volatile material" may also comprise other actives, such as sanitizers, air and/or fabric fresheners, cleaners, odor eliminators, mold or mildew inhibitors, insect repellents, and the like, or others that have aromatherapeutic properties. The "volatile material" alternatively comprises any fluid known to those skilled in the art that can be dispensed from a container, such as those suitable for dispersal in the form of particles or droplets suspended within a gas and/or propelled by means of a propellant. In one aspect, the "volatile material" may include one or more solvents, such as an organic or aqueous solution, in which an insect control agent may be dissolved. For example, in certain aspects, the active agent may be in a solid state at room temperature (23° C.), and a solvent may be added to the active agent in order to provide and keep the volatile material in a liquid state, thus allowing the volatile material to spread, be coated on, and positioned within a substrate, such as the sleeve or reservoir strip of the candles of the present disclosure. However, in other embodiments, the "volatile material" may not be mixed with any other components and may consist solely of the active agent.

The term "about," as used herein, refers to variation in the numerical quantity that may occur, for example, through typical measuring and liquid handling procedures used for making concentrates or use solutions in the real world, through inadvertent error in these procedures, through differences in the manufacture, source, or purity of the ingredients used to make the compositions or carry out the methods, and the like. The term "about" may also encompass amounts that differ due to different equilibrium conditions for a composition resulting from a particular initial mixture. In one embodiment, the term "about" refers to a range of values±5% of a specified value.

The terms "weight percent," "wt-%," "percent by weight," "% by weight," and variations thereof, as used herein, refer to the concentration of a substance or component as the weight of that substance or component divided by the total weight, for example, of the composition or of a particular component of the composition, and multiplied by 100. It is understood that, as used herein, "percent," "%," and the like may be synonymous with "weight percent" and "wt-%."

Volatile Material Dispenser/Candle

With reference to FIG. 1, a typical candle 100 includes a wax composition 102, a fragrance mixed in the wax composition 102, a wick 104 positioned in the wax composition 102, and a vessel or jar 106 for holding the wax composition 102 and the wick 104. Further, when a user lights the wick 104, the wax 102 burns and creates a pool of molten wax (not shown), which allows for the evaporation and emanation of the fragrance therein. However, as the wax 102 is burned or heated, the fragrance in the wax 102 is also burned, leading to the formation of soot and the emission of VOCs, such as benzene or naphthalene. The formation of soot and VOCs by the candle 100 occurs at least in part because of an incomplete combustion of the wax 102 in the flame of the candle 100.

In particular, when the wick 104 of the candle 100 is lit, the heat of the flame of the candle 100 melts the wax 102 near the wick 104, and then the liquid wax is drawn up the wick 104 by capillary action. The heat of the flame of the candle 100 vaporizes the liquid wax, turning it into a hot gas, and breaks down the hydrocarbons of the wax 102 into molecules of hydrogen and carbon. These vaporized molecules are then drawn up into the flame, where they react with oxygen from the ambient air to create heat, light, water vapor, and carbon dioxide. However, the combustion of the wax 102 and the fragrance therein is sometimes not a complete (e.g., fully stoichiometric or ideal) combustion. As a result, the candle 100 typically produces soot, i.e., a black powdery or flaky substance consisting largely of amorphous carbon produced by the incomplete burning of organic matter, like the hydrocarbon composition of the wax 102. In addition, the candle 100 can emit VOCs. VOCs are compounds that are composed primarily of carbon, oxygen, and hydrogen, which can evaporate into the air as the wax 102 and the fragrance therein burns and evaporates.

Unlike the typical candles depicted in FIG. 1, the candles of the present disclosure include a wax or fuel composition essentially free of, substantially free of, or devoid of a fragrance or active agent. Therefore, as the wax or fuel composition burns and melts, less soot and VOCs are emitted into the ambient or surrounding environment. Rather than mixing the fragrance or volatile material with the wax, the candles of the present disclosure include the fragrance, volatile material, or active agent in another element of the candle.

Figure 2:
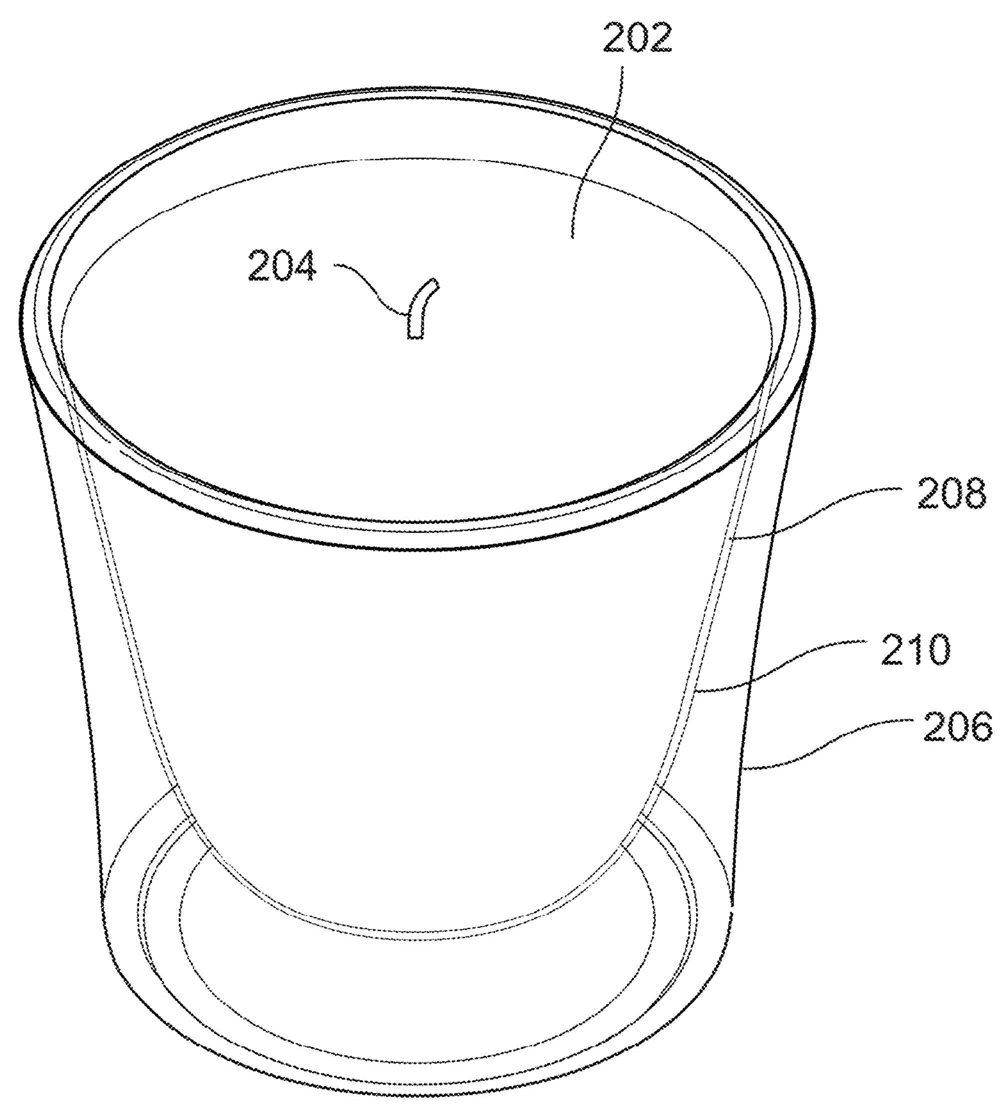
FIG. 2 is a perspective view of a candle, according to one aspect of the present disclosure.
Figures 3, 4:
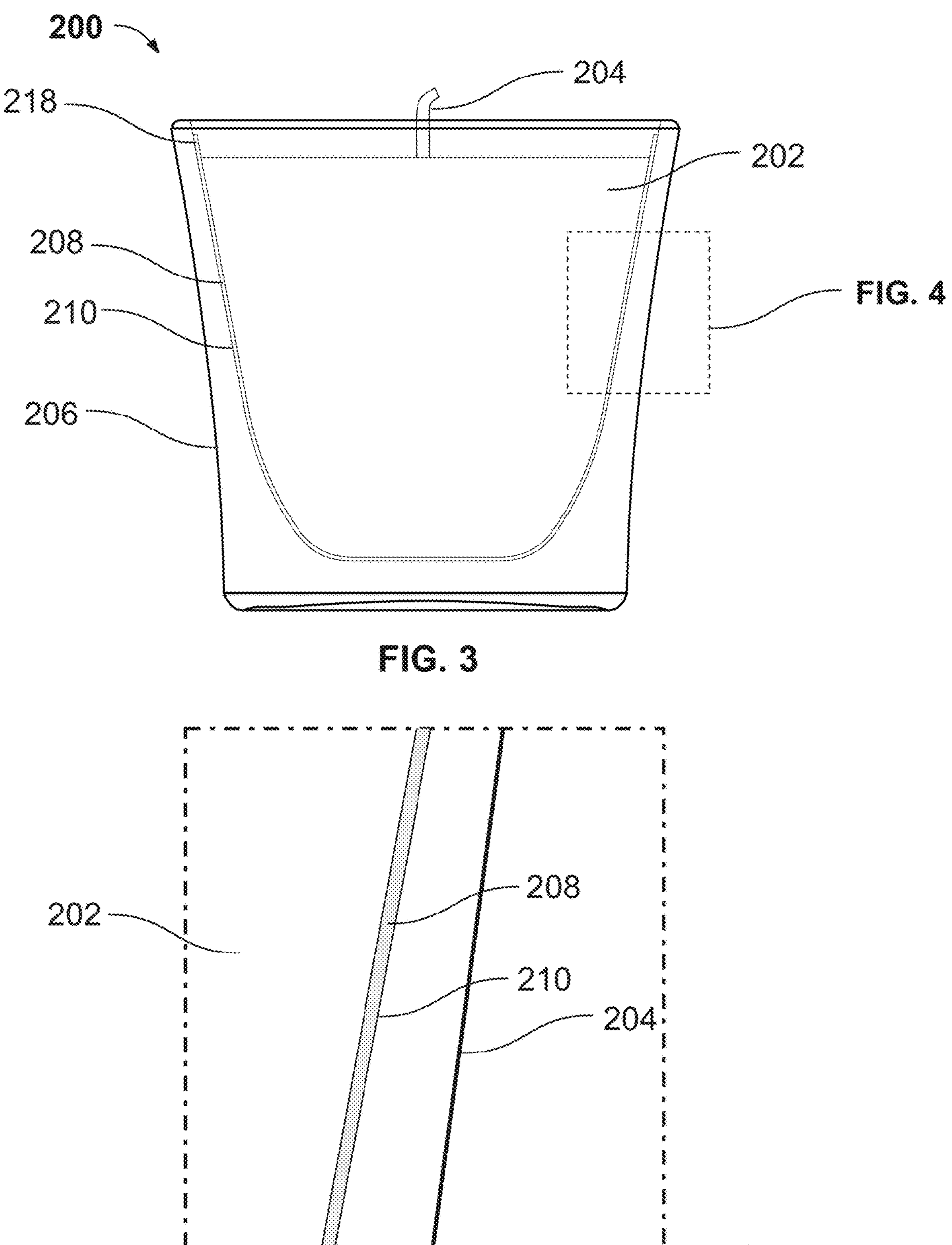
FIG. 3 is a front elevational view of the candle of FIG. 2.
FIG. 4 is a magnified view of a portion of the candle depicted in FIG. 3.
Figure 5:
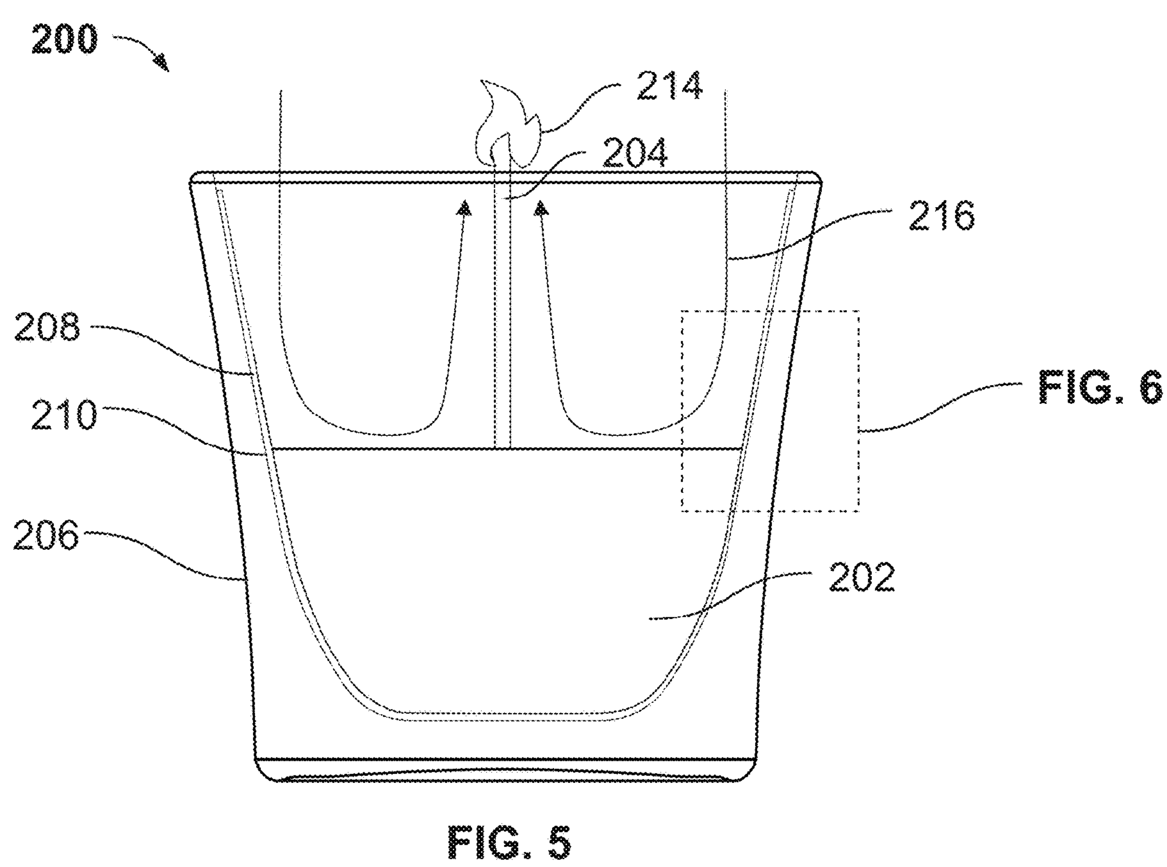
FIG. 5 is a front elevational view of the candle of FIG. 2 after a portion of the wax or fuel composition is burned and while the wick has an active flame.
Figure 6:
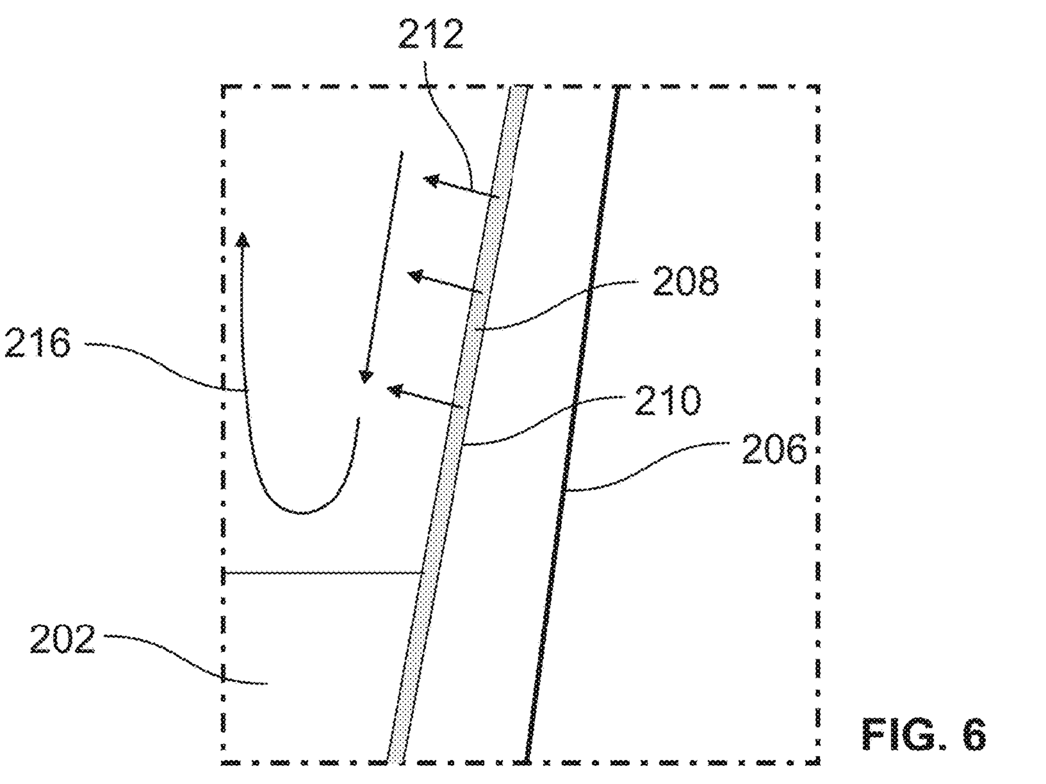
FIG. 6 is a magnified view of a portion of the candle depicted in FIG. 5.

For example, FIGS. 2-6 illustrate a candle 200 according to one aspect of the present disclosure, and as shown in FIGS. 2-4, the candle 200 includes a wax or fuel composition 202, a wick 204, ajar or vessel, shown as a container 206, and a volatile material sleeve or reservoir strip 208 positioned between at least a portion of an interior surface 210 of the container 206 and the wax or fuel composition 202. Therefore, unlike a typical fragrance candle (such as the candle 100), the fragrance from the candle 200 emanates from the sleeve or reservoir 208. In effect, as shown in FIGS. 5 and 6, the wax or fuel composition 202 of the candle 200 burns and melts, which causes the exposure of the sleeve or reservoir 208 and emanation and passive evaporation of the fragrance from the sleeve or reservoir 208 (as illustrated by arrows 212). Further, as the wax or fuel composition 202 burns and melts, more surface area of the sleeve or reservoir 208 becomes exposed to the ambient environment, allowing for continued emanation of the fragrance or volatile material from the candle 200. This may be referred to as the hot throw of the candle 200. In addition, as previously discussed herein, the flame of a candle (such as a flame 214 of the candle 200) heats the surrounding wax and nearby air. As the warm air from the candle 200 moves up, cooler air and oxygen rush in at the bottom of the flame 214 to replace the warmed air. Then, as that cooler air is heated by the flame 214, the cooler air rises as well and is replaced again by cooler air at a base of the flame 214. This air movement creates a continual cycle of upward movement of air (as illustrated by arrows 216) around the flame 214. This movement of air also creates a convection current, which acts to cause emanation of the fragrance, volatile material, or active agent from the sleeve or reservoir 208, as shown in FIGS. 5 and 6 by arrows 212. The heat from the flame 214 may also increase the emanation or evaporation of the volatile material or fragrance from the sleeve or reservoir 208, which may be referred to as the hot throw of the candle 200. The heat from the flame 214 can thereby create at least some amount of active evaporation of the fragrance, volatile material, or active agent. Further, as the fragrance, volatile material, or active agent is vapor or gaseous when it emanates from the sleeve or reservoir 208, it is not burnt in the flame 214. Therefore, unlike the candle 100, the fragrance, volatile material, or active agent of the candle 200 is not drawn up into the wick 204 by capillary action, and as a result, is not vaporized in the flame 214 with the wax composition 202. Thus, the combustion of the wax composition 202 by the flame 214 of the candle 200 is more efficient, which creates a cleaner flame that produces less soot and less VOCs.

As discussed herein, the fragrance or active agent of the candle 200 is not burnt in the flame during use because the fragrance or active agent is not in the wax or fuel composition 202. Rather, the fragrance, volatile material, or active agent is in the sleeve or reservoir 208, which is distinct from the wax composition 202 and is positioned away from the wick 204 and the flame 214 of the candle 200. As a result, since the interior wax or fuel composition 202 no longer has a fragrance or volatile material, the performance of the flame would be consistent because the fragrance or volatile material is known to affect the burn of the flame, such as the flame 214. In particular, the fragrance or volatile material can cause an inconsistent flame and may cause a disturbance in the flame 214 of the candle 200, which leads to the incomplete combustion of the wax or fuel composition 202 and the formation of soot and VOCs. Having a wax or fuel composition 202 devoid, essentially free of, or substantially free of a fragrance or volatile material eliminates these disturbances and creates a more consistent flame, such as the flame 214, that more completely burns the wax or fuel composition 202. Thus, the candle 200 emits less soot and/or VOCs as compared to a traditional candle, like the candle 100. Even further, the candle 200 provides a more effective and improved fragrance intensity, as the fragrance will not have a smoky character, for example, and will not be burnt off prior to release. As such, the smell and delivery of the fragrance or active agent is cleaner and stronger as compared to a traditional candle of the prior art. In addition, the candle 200 provides a more consistent burn than traditional candles because the flame 214 produced by burning a composition of wax that is substantially free of volatile compounds reduces variability in the combustion process taking place on the one or more wicks of the candle 200. A wide variety of fragrances and other active or volatile compounds can be used within the candle 200 without significantly impacting the combustion process of the candle 200.

The sleeve or reservoir 208 of the candle 200 may include a permeable material, which allows for air and liquid to freely pass through or otherwise release from the sleeve or reservoir 208. Permeable surfaces and materials are those that contain pores or openings that allow liquids and gases to pass therethrough. For example, in particular embodiments, the sleeve or reservoir 208 may be constructed from a substrate or a material that properly acts as a reservoir for the fragrance, volatile material, or active agent. Specifically, the sleeve or reservoir strip 208 may be constructed from a material that can optimally absorb and store a fragrance, volatile material, or active agent without degrading or decomposing. For example, the sleeve or reservoir 208 may be a fibrous material or fabric, and may be constructed from a cotton, polyester, rayon or nylon-based material, or combinations thereof. In further embodiments, the sleeve or reservoir 208 may include at least one or more materials that act as a barrier layer to the volatile material stored therein. That is, the sleeve or reservoir 208 may include at least one or more materials configured to be rate-limiting for mass-transport of the fragrance, volatile material, or active agent from the dispensing device or candle 200. More particularly, the sleeve or reservoir 208 may be a reservoir layer formed by one or more materials that are permeable to the fragrance, volatile material, or active agent therein, as well as rate-limiting to the volatile material to emit the volatile material at a desired rate of emission. In other words, the sleeve or reservoir 208 may be constructed from a material that is compatible with the volatile material such that the volatile material is readily stored within the sleeve or reservoir 208 when the candle 200 is in a non-active state (i.e., when the candle 200 is not lit), yet allows for emanation of the volatile material or fragrance when the wick 204 is ignited and the flame 214 is present. In some examples, the sleeve or reservoir 208 is formed from a consumable material that releases the fragrance as it is consumed (e.g., melts, evaporates, etc.) As such, the sleeve or reservoir 208 may control the emanation rate or rate of evaporation of the volatile material from the candle 200.

The sleeve or reservoir 208 may also be constructed from a material that is particularly compatible with the fragrance, volatile material, or active agent used in the candle 200. For example, in one specific embodiment, the material of the sleeve or reservoir 208 may be ethylene vinyl acetate and the volatile material may be transfluthrin. Examples of materials that are satisfactory for forming the sleeve or reservoir may also include a nylon or nylon-based film, a polysulfone (PSU), an acrylonitrile butadiene styrene (ABS), a styrene-acrylonitrile (SAN), a polyethylene (PE), a poly(p-phenylen oxide) (PPO), a polybutylene terephthalate (PBT), a polyvinyl chloride (PVC), a polyester film a polycarbonate (PC), a styrene-butadiene (SBR), a polyethylene terephthalate glycol (PETG), a poly(methyl methacrylate) (PMMA), a polyvinyl alcohol (PVOH), a polystyrene (PS), a polypropylene (PP), a polyethylene terephthalate (PET), a polyethylene terephthalate/polyethylene naphthalate copolymer (PET-PEN), an ethylene-vinyl acetate (EVA), a poly(ether sulfones) (PES), an acrylonitrile-methyl acrylate copolymer (e.g., Barex® 210), a high-density polyethylene (HDPE), an ethylene vinyl alcohol (EVOH), a polyacetal or a polyoxymethylene (POM), a polyethylene glycol (PEO), an ethylene (meth)acrylic acid (EAA, EMAA) (e.g., Surlyn®), cellophane, and/or polyacrylonitrile (PAN), and/or a combination or metalized form thereof.

In one aspect, the sleeve or reservoir 208 may be formed from a polyethylene (PE), a polyvinyl alcohol (PVOH), a polypropylene (PP), an ethylene-vinyl acetate (EVA), such as an ethylene-vinyl acetate resin under the trade name Elvax®, a high-density polyethylene (HDPE), and/or an ethylene vinyl alcohol (EVOH), or blends of these materials. The sleeve or reservoir 208 may also be formed of EZ Peel® EVA or PE co-extruded sealant.

The sleeve or reservoir 208 may also have a thickness and can be a relatively thin layer with a thickness ranging between about 10 μm and about 20 mm, about 10 μm and about 10 mm, about 10 μm and about 1 mm, about 10 μm and about 250 μm, or between about 50 μm and about 100 μm, or between about 75 μm and about 90 μm.

In other embodiments, the sleeve or reservoir 208 may be comprised of terracotta, concrete, or wood. For example, the sleeve or reservoir 208 may include wood, such as a sandalwood, a cedar, a patchouli, a vetiver, a cypress, an oud wood, a guaiac wood, and/or a birch wood. In other embodiments, the sleeve or reservoir 208 may include a terracotta material or a clay-based unglazed or glazed ceramic where the fired body is porous. In further embodiments, the sleeve or reservoir 208 may be constructed from a natural polymer, such as a cellulose nanocystal (CNC).

Figure 7:
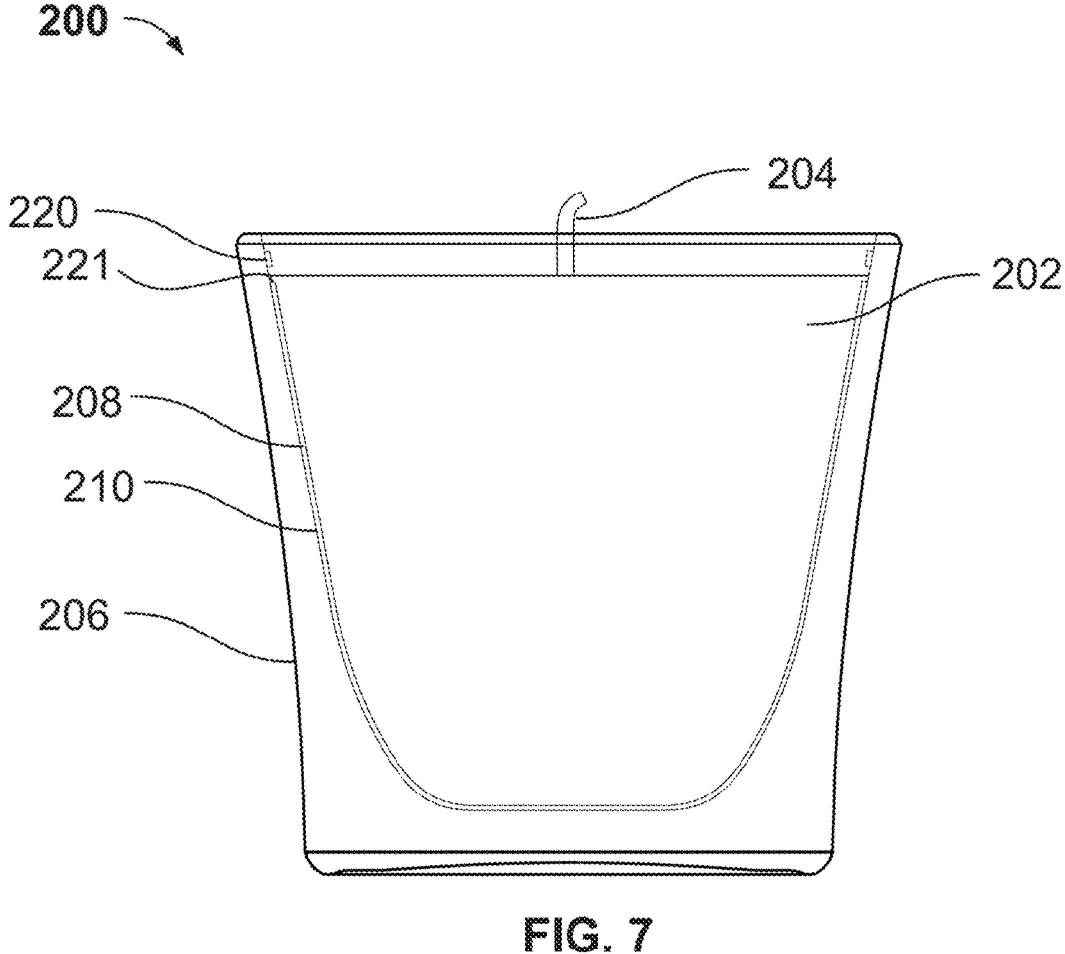
FIG. 7 is a front elevational view of another candle, according to another aspect of the present disclosure.

With specific reference to FIG. 3, an upper portion 218 of the sleeve or reservoir 208 may also be exposed to the ambient environment before the wax or fuel composition 202 is burned and before any wax melts. As a result, the sleeve or reservoir 218 can still provide a cold throw, which is the passive emanation of the fragrance, volatile material, or active agent before the wax or fuel composition 202 is burned, thereby allowing a user or customer to smell the fragrance of the candle 200 before purchasing and using the candle 200. In an alternative embodiment, as shown in FIG. 7, the candle 200 may include a second sleeve or reservoir 220 that is exposed to the ambient environment prior to lighting the wick 204 and the sleeve or reservoir 208 is not exposed to the ambient or surrounding environment prior to lighting the wick 204. Rather, in this embodiment, the wax or fuel composition 202 of the candle 200 acts as a barrier to prevent the fragrance, volatile material, or active agent in the sleeve or reservoir 208 from emanating therefrom prior to use by completely encapsulating the sleeve or reservoir 208 between the wax or fuel composition 202 and the vessel or container 206 of the candle 200. Then, when the wick 204 is lit and the wax or fuel composition 202 begins to burn, the top layer of the wax or fuel composition 202 will melt, thereby exposing the sleeve or reservoir 208 (including an upper end 221 thereof) to the ambient environment and allowing emanation of the fragrance or volatile material therefrom. In further embodiments, the candle 200 may also include a cap or lid (not shown) that could be used to halt the continued loss of fragrance or volatile material over time when on the store shelf. In still other embodiments, the upper end 221 of the sleeve or reservoir 208 may be coated or otherwise comprise a non-permeable material that prevents the diffusion of the fragrance or volatile material. In yet other embodiments, the non-permeable coating or material may be burnt or melted off upon activation of the candle 200.

Figures 8, 9:
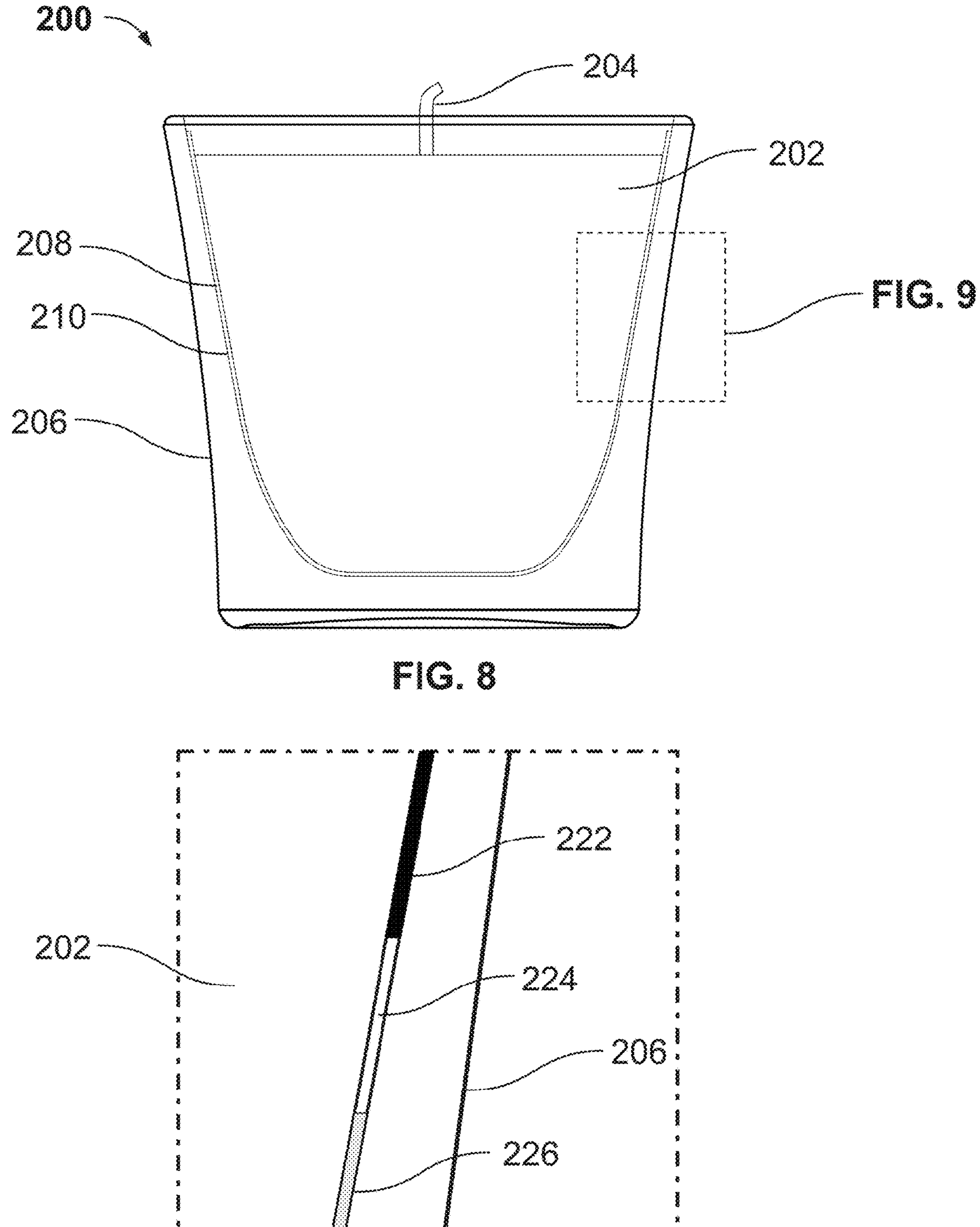
FIG. 8 is a front elevational view of another candle, according to yet another aspect of the present disclosure.
FIG. 9 is a magnified view of a portion of the candle depicted in FIG. 8.
Figure 10:
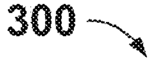
FIG. 10 is a perspective view of a candle, according to another aspect of the present disclosure.
Figure 10:
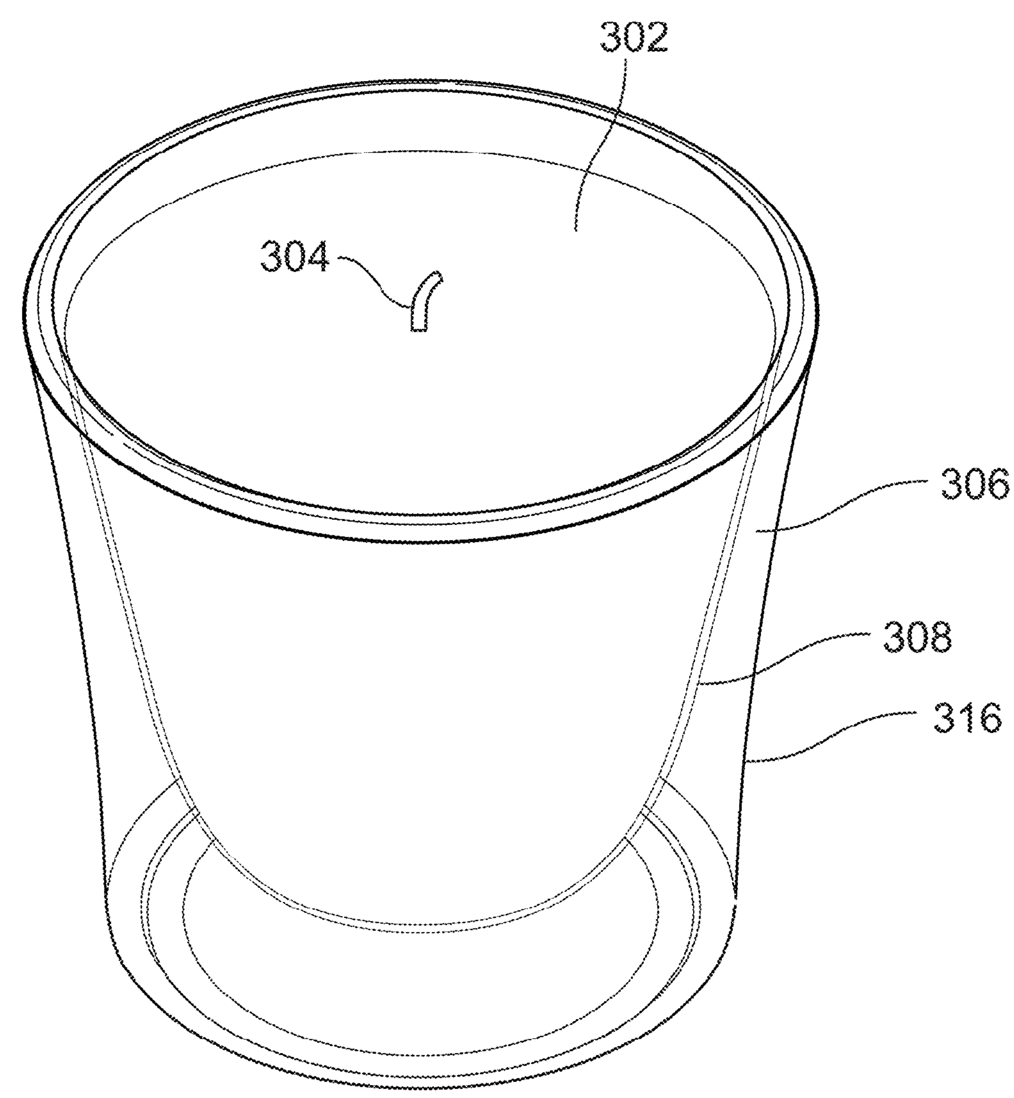
Figures 11, 12:
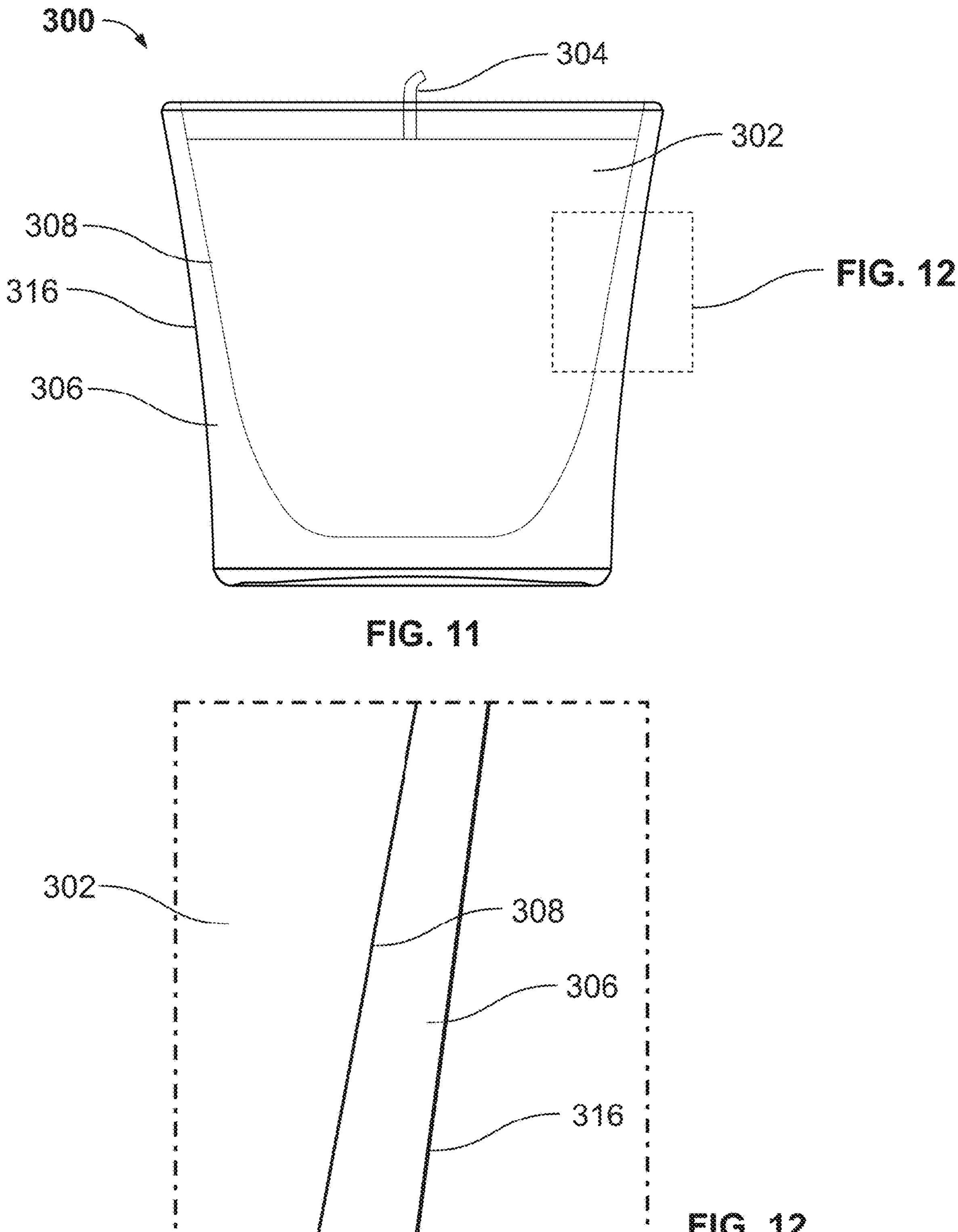
FIG. 11 is a front elevational view of the candle of FIG. 10.
FIG. 12 is a magnified view of a portion of the candle depicted in FIG. 11.

FIGS. 8 and 9 illustrate the candle 200 according to another aspect of the present disclosure. As shown in FIGS. 8 and 9, the candle 200 includes the wax or fuel composition 202, the wick 204, the vessel or container 206, and the volatile material sleeve or reservoir 208 positioned between at least a portion of the interior surface 210 of the container 206 and the wax or fuel composition 202. However, in this embodiment, the sleeve or reservoir 208 of the candle 200 includes several layers, including an upper layer 222, a middle layer 224, and a lower layer 226. Additionally, although this particular embodiment of the candle 200 includes a sleeve or reservoir with three layers, the sleeve or reservoir 208 can include any number of layers, including two layers, three layers, four layers, five layers, six layers, etc.

The layers 222, 224, 226 of the sleeve or reservoir 208 can provide alternative effects during use. For example, the layers 222, 224, 226 may include different fragrances or volatile materials. As a result, the candle 200 may provide numerous fragrances to a user during its use. More particularly, in one specific embodiment, the upper layer 222 may include a first fragrance, the middle layer 224 may include a second fragrance, and the lower layer 226 may include a third fragrance. Therefore, the candle 200 may emit the first fragrance after a top portion of the wax or fuel composition 202 burns or melts, the second fragrance after a middle portion of the wax or fuel composition 202 burns or melts, and the third fragrance after a lower portion of the wax or fuel composition 202 burns or melts. Alternatively, the layers 222, 224, 226 of the candle 200 can include the same fragrance or volatile material, but the fragrance or volatile material may be included in different concentrations or dosages. For example, the upper layer 222 may include the fragrance or volatile material at a first dosage, the middle layer 224 may include the fragrance or volatile material at a second dosage that is larger than the first dosage, and the lower layer 226 may include the fragrance or volatile material at a third dosage that is larger than the second dosage. This embodiment may be useful when the fragrance or volatile material is known to decrease over time. In these circumstances, the lower layers (such as the middle layer 224 and the lower layer 226) may include a higher dosage of the fragrance or volatile material because these layers are exposed to the ambient environment later than the upper layers of the sleeve or reservoir 208 (such as the upper layer 222). Thus, the lower layers of the sleeve or reservoir 208 include higher concentrations of the fragrance or volatile material, such that the user experience is uniform or relatively constant throughout the lifetime of the candle 200.

According to another embodiment, the upper layers (such as the upper layer 222 and the middle layer 224) may include a higher dosage of the fragrance or volatile material because these layers are exposed to the ambient environment first, and as such, must emanate the fragrance, volatile material, or active agent over a longer period. Therefore, to allow for constant emanation over the life of the candle 200, the upper layers of the sleeve or reservoir 208 may include higher concentrations of the fragrance volatile material, or active agent, such that the user experience is uniform or relatively constant through the lifetime of the candle 200. In addition, as a wax or fuel composition burns and melts, more surface area of the sleeve or reservoir 208 is exposed. Therefore, to allow for a relatively constant emanation rate, the upper layers of the sleeve or reservoir 208 may include higher concentrations, such that when there is less surface area of the sleeve or reservoir 208 exposed to the ambient environment, there is relatively the same emanation rate compared to later when additional surface area of the sleeve or reservoir 208 is exposed as the wax or fuel composition 202 burns or melts. In short, the ability to selectively increase or decrease the fragrance, volatile material, or active agent dosage levels across layers of the sleeve or reservoir 208 allows the candle 200 to be optimized such that habituation does not occur and a user continues to experience the fragrance, volatile material, or active agent over the lifetime of the candle 200.

Further embodiments of the present disclosure provide a candle where the layers 222, 224, 226 may be made from alternative materials. For example, as previously discussed herein, the sleeve or reservoir 208 may be constructed from numerous materials, such as terracotta, concrete, wood, various cloth materials, or plastics. In this embodiment, the upper layer 222 may be constructed from a first material (e.g., terracotta, wood, a cloth, a substrate, etc.), the middle layer 224 may be constructed from a second material, and the lower layer 226 may be constructed from a third material. The materials for the layers 222, 224, 226 may be chosen based on a combination of factors. For example, the layers 222, 224, 226 may include different fragrances or volatile materials or different dosages of fragrances or volatile materials, as previously discussed herein. With that in mind, the materials of the layers 222, 224, 226 may be optimally chosen based on the specific fragrance or dosage or concentration of the fragrance or volatile material for the layer. For example, a first fragrance or volatile material and first dosage therefor may be chosen for the upper layer 222, and then the material for the upper layer 222 may be chosen to optimally store and emanate the first fragrance or volatile material. Further, the second fragrance or volatile material and second dosage therefor may be chosen for the middle layer 224, the material for the middle layer 224 may then be chosen, the third fragrance or volatile material and third dosage therefor may be chosen for the lower layer 226, and the material for the lower layer 226 may then be chosen.

In other embodiments, the sleeve or reservoir 208, as well as the layers 222, 224, 226 thereof, may provide a visible or aesthetic impression to a user. For example, in one embodiment, the upper layer 222 may be a first color, the middle layer 224 may be a second color, and the lower layer 226 may be a third color. According to another embodiment, the sleeve or reservoir 208 may be a first color when the sleeve or reservoir 208 is dosed or primed with the fragrance, volatile material, or active agent, and then transition to a second color once the fragrance, volatile material, or active agent emanates from or leaves the sleeve or reservoir 208. According to yet another aspect, the color or appearance of the sleeve or reservoir 208 may change or transition during use of the candles 200, 300 to provide an aesthetic effect to the candles 200, 300 (such as by providing a visually pleasing appearance or color transition) and/or a function effect to the candles 200, 300 (such as by providing a visual indication that the sleeve or reservoir 208 is devoid of the fragrance, volatile material, or active agent).

Further, in some embodiments, the sleeve or reservoir 208 may include several strips or reservoirs positioned along the interior surface 210 of the container 206. In such embodiments, the wax or fuel composition 202 may also be adjacent to the interior surface 210 where the sleeve or reservoir 208 is not present. For example, in these embodiments, the sleeve or reservoir 208 may include a reservoir positioned every 60 degrees, 90 degrees, 120 degrees, or 180 degrees around a circumference of the interior surface 210 of the container 206. In other embodiments, the reservoirs may be positioned along the interior surface 210 at a location radially outward from the wick 204. Further, in embodiments where the candle 200 includes multiple wicks, the reservoirs may be positioned along the interior surface 210 at a location radially outward from a center of the candle and the wicks of the candle. For example, if a candle includes three wicks in a triangular formation, the candle may include three reservoirs: one reservoir positioned at a location radially outward from a center of the container and a first wick, one reservoir positioned at a location radially outward from the center of the container and a second wick, and one reservoir positioned at a location radially outward from the center of the container and a third wick.

FIGS. 10-14 depict another embodiment of a candle 300, according to another aspect of the present disclosure. As shown in FIGS. 10-14, the candle 300 of this embodiment includes a wax or fuel composition 302, a wick 304, and a vessel or container 306. Like the candles 200 previously described herein, the wax or fuel composition 302 of the candle 300 is devoid of, substantially free of, or essentially free of a fragrance, volatile material, or active agent. Rather than being placed in the wax or fuel composition 302, the fragrance or volatile material of this embodiment is present in the vessel or container 306. More particularly, the vessel or container 306 of the present embodiment is at least partially constructed from a material that is at least partially permeable or porous and the fragrance, volatile material, or active agent emanates from the vessel or container 306.

Figure 13:
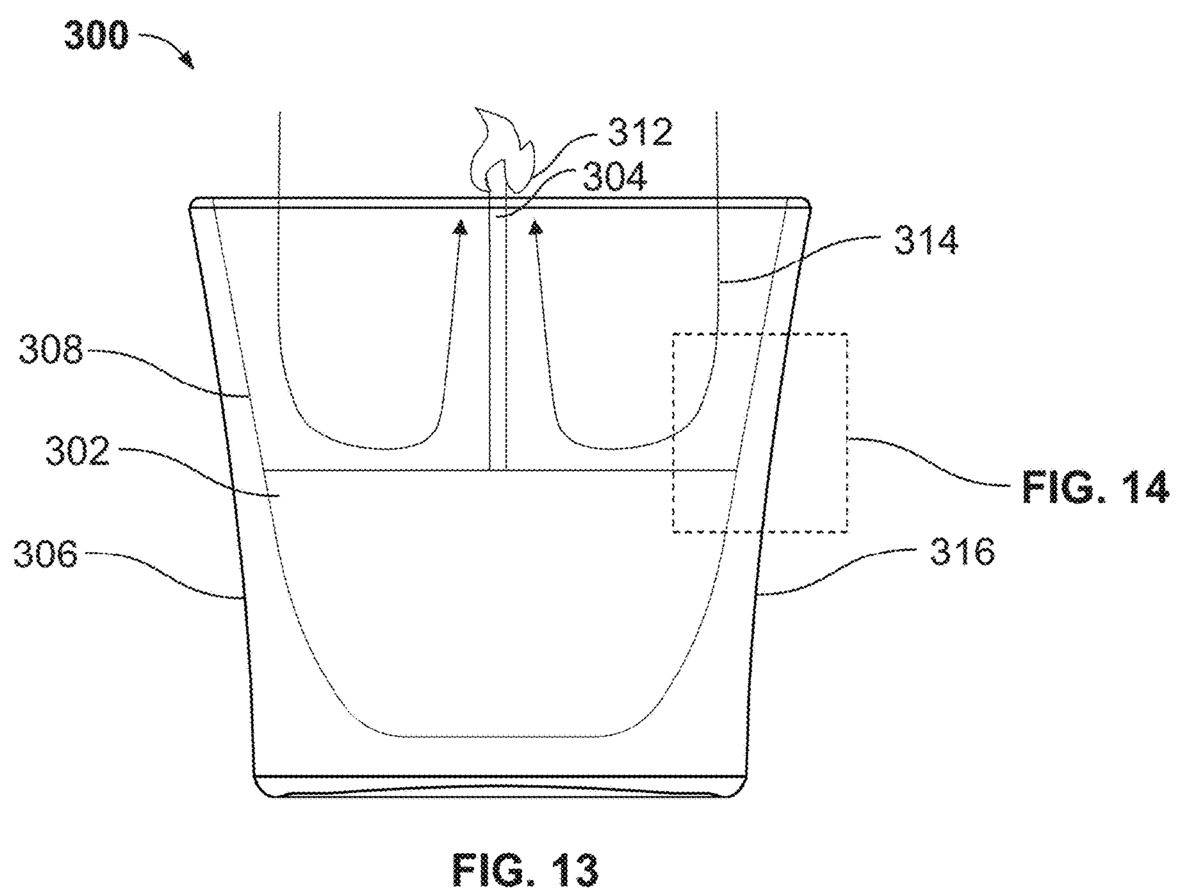
FIG. 13 is a front elevational view of the candle of FIG. 10 after a portion of a wax or fuel composition of the candle is burned and while the wick has an active flame.
Figure 14:
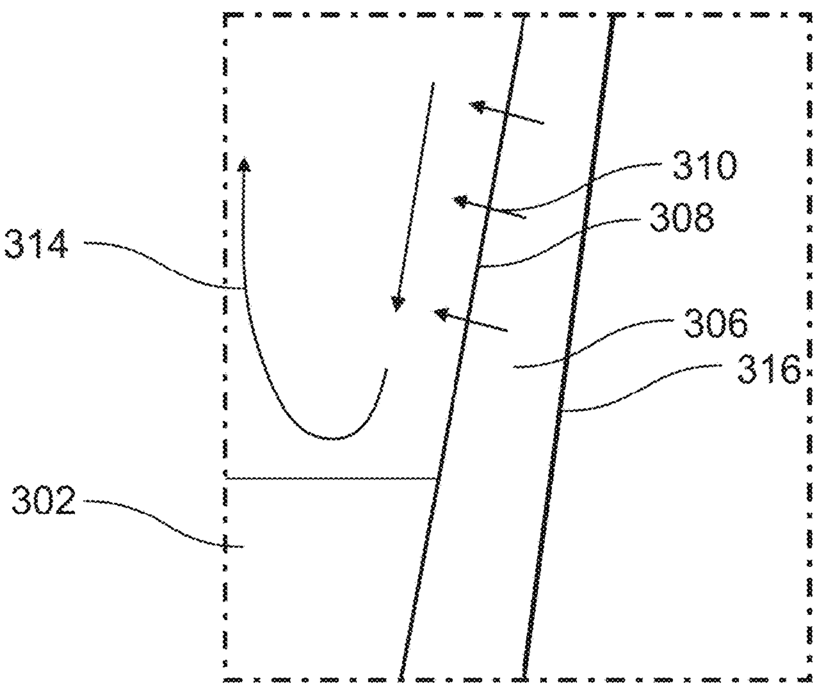
FIG. 14 is a magnified view of a portion of the candle depicted in FIG. 13.

Similar to the other embodiments discussed herein, a user may ignite the wick 304 of the candle 300 during use and cause the wax or fuel composition 302 to burn and melt. Further, as the wax or fuel composition 302 burns and melts, portions of an interior wall 308 of the candle 300 are exposed to the ambient and surrounding environment, which causes emanation or passive evaporation of the fragrance, volatile material, or active agent therefrom (as illustrated by arrows 310 in FIG. 14). This may be referred to as the hot throw of the candle 300. In addition, like the embodiments previously discussed herein, a flame 312 of the candle 300 can heat the surrounding wax and nearby air, and as air from the candle 300 moves up, cooler air and oxygen will begin to rush in at the bottom of the flame to replace the warmed air (as illustrated by arrows 314 in FIGS. 13 and 14). Then, as that cooler air is heated by the flame 312, the cooler air rises as well and is replaced again by cooler air at a base of the flame 312. This air movement creates a continual cycle of upward movement of air, as illustrated by arrows 314 around the flame 312. This movement of air also creates a convection current that further assists in the emanation of the fragrance, volatile material, or active agent from the vessel or container 306, as shown in FIGS. 13 and 14. The heat from the flame 312 may also increase the emanation or evaporation of the volatile material or fragrance from the vessel or container 306. The heat from the flame 312 can thereby create at least some amount of active evaporation of the fragrance, volatile material, or active agent. Even further, the fragrance, volatile material, or active agent is not drawn up into the wick 304 and the flame 312 by capillary action because the fragrance, volatile material, or active agent is vapor or gaseous when it emanates or leaves the vessel or container 306. As such, the combustion of the wax or fuel composition 302 by the flame 312 of the candle 300 is more efficient, creates a cleaner flame, and produces less soot and VOCs. Additionally, as the fragrance, volatile material, or active agent is not burned in the flame 312, the smell and delivery of the fragrance or volatile material is cleaner and stronger than traditional candles of the prior art.

In this embodiment, an exterior wall 316 of the vessel or container 306 is also sealed to prevent premature emanation and evaporation of the fragrance or volatile material from the candle 300. More particularly, the vessel or container 306 is constructed from a material that is porous or permeable, but the exterior wall 316 of the vessel or container 306 is sealed by a means to prevent the fragrance from seeping through to the outside of the container 306 and emanating therefrom prior to a user igniting the wick 304 and the wax or fuel composition 302 melting. In one embodiment, the vessel or container 306 is constructed from a terracotta, clay, or ceramic material and the exterior wall 316 of the candle 300 can be sealed by a glazing process where the exterior wall 316 is glazed with a glass coating, for example. The glaze can take many forms. For example, the glaze can be transparent, may include a metal additive, can be colored, textured, glossy, matte, opaque, etc.

In another embodiment, the exterior wall 316 may be coated with a solvent resistant coating. For example, the exterior wall 316 may include a sealant layer thereon that is a polyethylene terephthalate (PET), an ethylene-vinyl acetate (EVA), a polyethylene, such as a low-density polyethylene (LDPE), a high molecular weight low-density polyethylene, or a linear low-density polyethylene (LLDPE), a polypropylene (PP), ethylene-butene copolymer, polybutene, butylene copolymers, an ethylene vinyl alcohol copolymer (EVOH), a polyester, a polyethylene terephthalate glycol (PETG), a polylactic acid (PLA), or a nylon. Combinations or blends (e.g., binary or ternary blends) of the aforementioned materials may also be used. For example, blends which may be used for the sealant layer are EVA-LDPE, polybutene-EVA, polybutene-LDPE-EVA, etc. Other materials that may be suitable for use as the sealant layer on the exterior wall 316 include one or more polyethylene terephthalate film structures, such as transparent films under the trade names EZ Peel®, Mylar®, e.g., Mylar® OL, LumiLid®, e.g., Lumilid® XL 7, Lumirror®, e.g., Lumirror® XL 5, or Curlon®, all of which are either provided by DuPont, Toray Industries, Inc. or Bemis Company, Inc. In a further embodiment, the sealant layer may be CURLON® (Grade A9599) and W18-000832 from Bemis Company, Inc. According to another embodiment, the sealant layer may be a polysiloxane coating layer. For example, U.S. Pat. No. 10,472,526, issued on Nov. 12, 2019, and titled "Peelable Surface Coating System Over Multi-Section Substrate" discloses coatings and sealers, including the potential materials that can be used for coatings and sealers. U.S. Pat. No. 10,472,526 is incorporated herein by reference in its entirety.

The interior wall 308 may also be partially glazed or sealed to affect the evaporation and emanation of the fragrance as the candle burns. In these embodiments, the same materials used to glaze or seal the exterior wall 316 may be used to partially seal the interior wall 308 of the vessel or container 308.

In this embodiment, the vessel or container 306 is at least partially constructed from a permeable or porous material, which allows for gas and liquid to freely pass through the vessel or container 306. As discussed previously herein, permeable surfaces and materials are those that contain pores or openings that allow liquids and gases to pass therethrough. For example, in particular embodiments, the vessel or container 306 may be constructed from a material that properly acts as a reservoir for the fragrance, volatile material, or active agent. Specifically, the vessel or container 306 may be constructed from a material that can optimally absorb and store a fragrance, volatile material, or active agent without degrading or decomposing. For example, the vessel or container 306 may be a fibrous material or fabric, and may be constructed from a cotton, polyester, rayon or nylon-based material, or combinations thereof. In further embodiments, the vessel or container 306 may include at least one or more materials that act as a barrier layer to the volatile material stored therein. For example, the vessel or container 306 may be constructed from a material that is compatible with the volatile material such that the volatile material is readily stored within the vessel or container 306 when the candle 300 is in a non-active state (i.e., when the candle 300 is not lit), yet also allows for emanation of the volatile material or fragrance when the wick 302 is ignited and the flame 312 is present. As such, the vessel or container 306 can control the emanation rate or rate of evaporation of the volatile material from the candle 300.

In some embodiments, the vessel or container 306 includes a terracotta, clay, or ceramic material. In other embodiments, the vessel or container 306 includes a concrete material. Still further, in some embodiments, the vessel or container 306 includes wood. For example, the vessel or container 306 may include a sandalwood, a cedar, a patchouli, a vetiver, a cypress, an oud wood, a guaiac wood, and/or a birch wood. In further embodiments, the vessel or container 306 may be constructed from a natural polymer, such as a cellulose nanocystal (CNC).

In some embodiments, the vessel or container 306 may be constructed from ethylene vinyl acetate and the volatile material may be transfluthrin. Further examples of materials that may be used for the vessel or container 306 include a polysulfone (PSU), an acrylonitrile butadiene styrene (ABS), a styrene-acrylonitrile (SAN), a polyethylene (PE), a poly(p-phenylen oxide) (PPO), a polybutylene terephthalate (PBT), a polyvinyl chloride (PVC), a polyester film, a polycarbonate (PC), a styrene-butadiene (SBR), a polyethylene terephthalate glycol (PETG), a poly(methyl methacrylate) (PMMA), a polyvinyl alcohol (PVOH), a polystyrene (PS), a polypropylene (PP), a polyethylene terephthalate (PET), a polyethylene terephthalate/polyethylene naphthalate copolymer (PET-PEN), an ethylene-vinyl acetate (EVA), a poly(ether sulfones) (PES), an acrylonitrile-methyl acrylate copolymer (e.g., Barex® 210), a high-density polyethylene (HDPE), an ethylene vinyl alcohol (EVOH), a polyacetal or a polyoxymethylene (POM), a polyethylene glycol (PEO), an ethylene (meth)acrylic acid (EAA, EMAA) (e.g., Surlyn®), a cellophane, and/or polyacrylonitrile (PAN), and/or a combination or metalized form thereof.

Figures 15, 16:
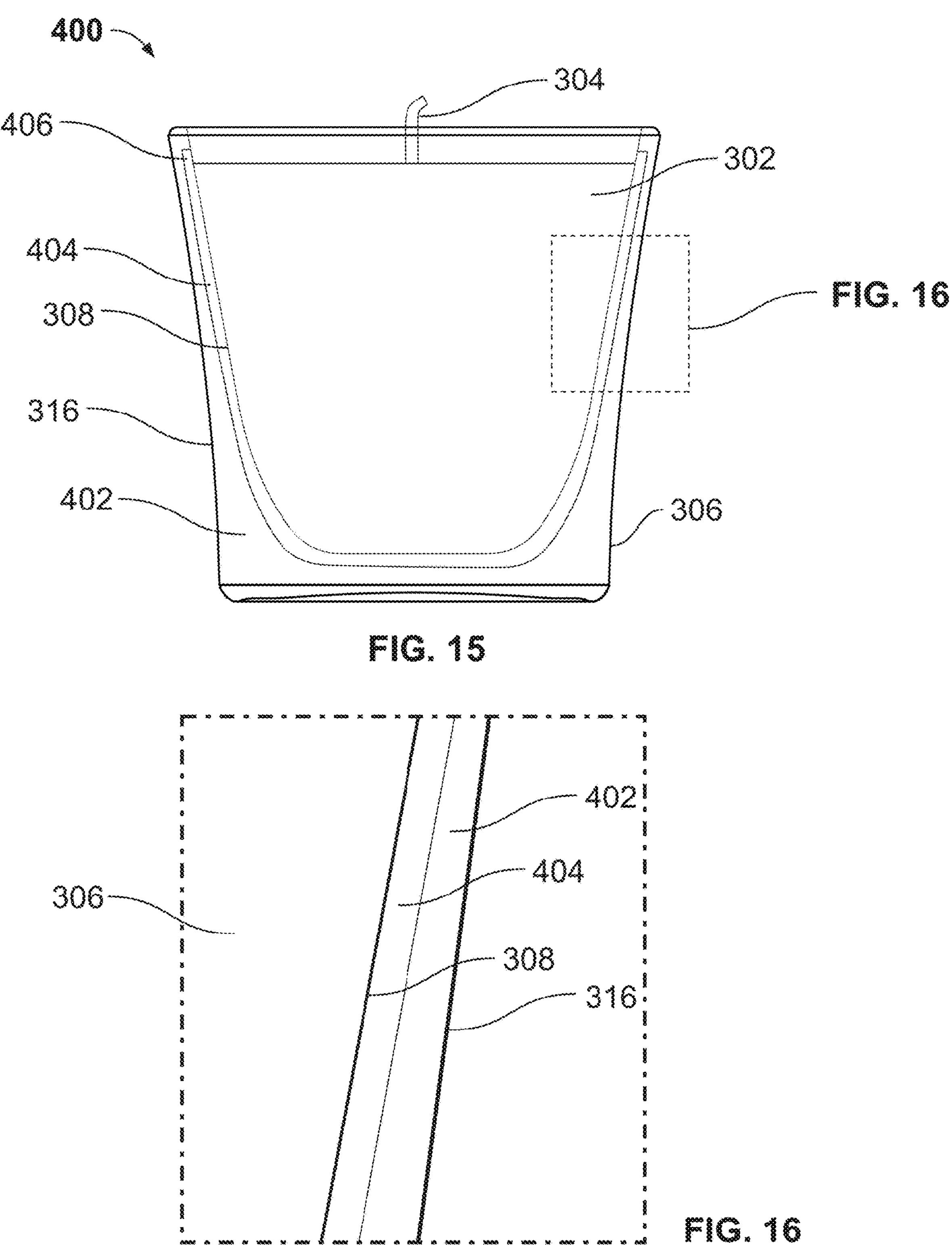
FIG. 15 is a front elevational view of yet another candle, according to yet another aspect of the present disclosure.
FIG. 16 is a magnified view of a portion of the candle depicted in FIG. 15.

FIGS. 15 and 16 depict another embodiment of a candle 400. In this embodiment, the vessel or container 306 includes a first portion 402 and a second portion 404. Further, the second portion 404 acts as a reservoir for a volatile material, a fragrance, or active agent, and the volatile material, fragrance, or active agent emanates from the second portion 404 during use of the candle 400. The first portion 402, on the other hand, acts to encapsulate or store the second portion 404 of the candle 400 and prevent premature emanation of the volatile material, fragrance, or active agent from the candle 400. For example, with reference to FIGS. 15 and 16, the second portion 404 is seated in the first portion 402 of the candle 400 and the second portion 404 is positioned between the first portion 402 and the wax composition 302 of the candle 400 prior to use. As such, the wax composition 302 and the first portion 402 of the candle 400 suppress or prevent the emanation of the volatile material, fragrance, or active agent from the second portion 404. With that said, an upper portion 406 of the second portion 404 may extend above the wax composition 302, as shown in FIG. 15, which allows for partial emanation of the volatile material, fragrance, or active agent from the second portion 404 prior to use of the candle 400. As discussed previously herein, this upper portion 406 of the second portion 404 may provide a cold throw to the candle 400, thereby allowing a customer or user to smell the volatile material or fragrance prior to purchasing the candle 400.

In this embodiment, the second portion 404 of the candle 400 can be constructed from any of the aforementioned materials discussed above in connection with the vessel or container 306 of the candle 300 depicted in FIGS. 10-14. For example, the second portion 404 of the candle 400 may be constructed from a terracotta, clay, or ceramic material. Alternatively, or in addition, the second portion 404 of the candle 400 may be constructed from a porous cement material, wood, a natural or synthetic polymer, or any of the other suitable materials previously discussed herein in connection with the container 306 of the candle 300. Additionally, the second portion 404 of the candle 400 may be constructed from numerous materials and may include numerous layers, like the sleeve or reservoir 208 shown in FIGS. 8 and 9 of the present disclosure. For example, similar to the sleeve or reservoir 208 shown in FIGS. 8 and 9 of the present disclosure, the second portion 404 of the candle 400 may include an upper portion or layer constructed from a first material and including a first volatile material, a middle portion or layer constructed from a second material and including a second volatile material, and a lower portion or layer constructed from a third material and including a third volatile material.

Figure 17:
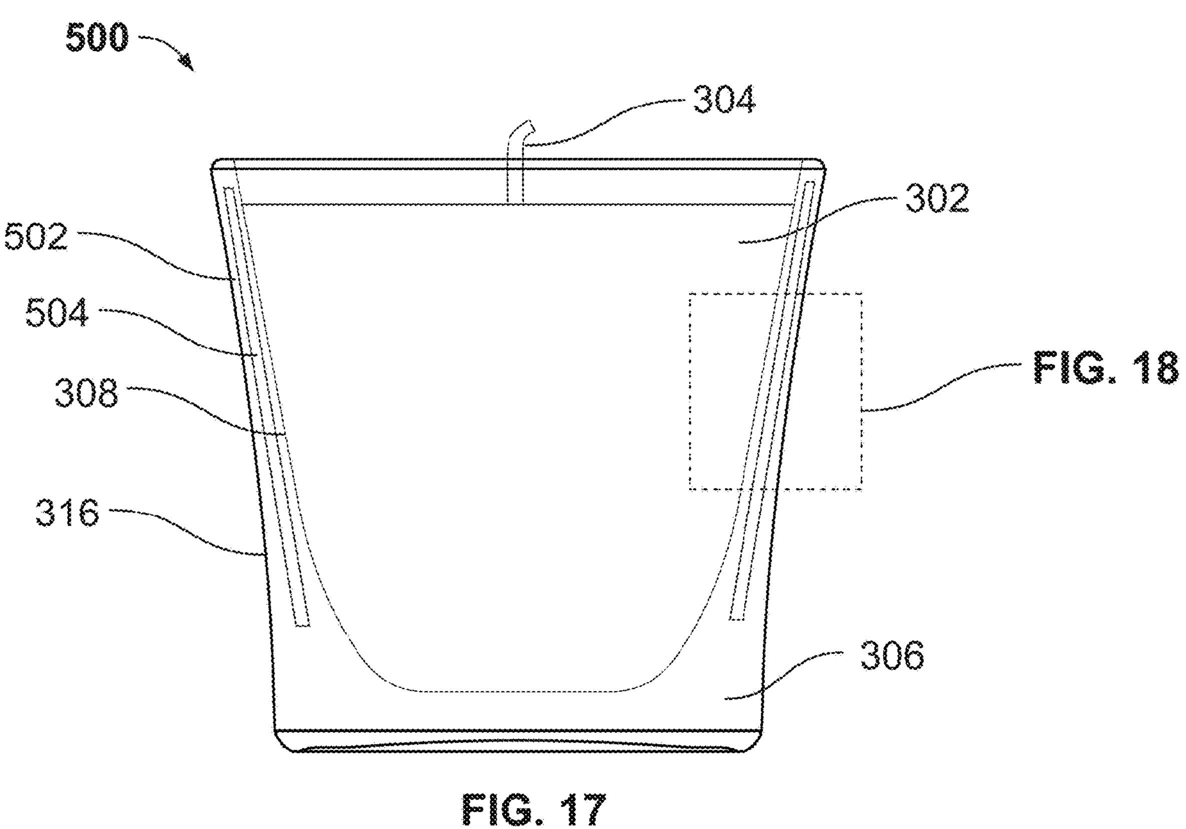
FIG. 17 is a front elevational view of another candle, according to a further aspect of the present disclosure.
Figure 18:
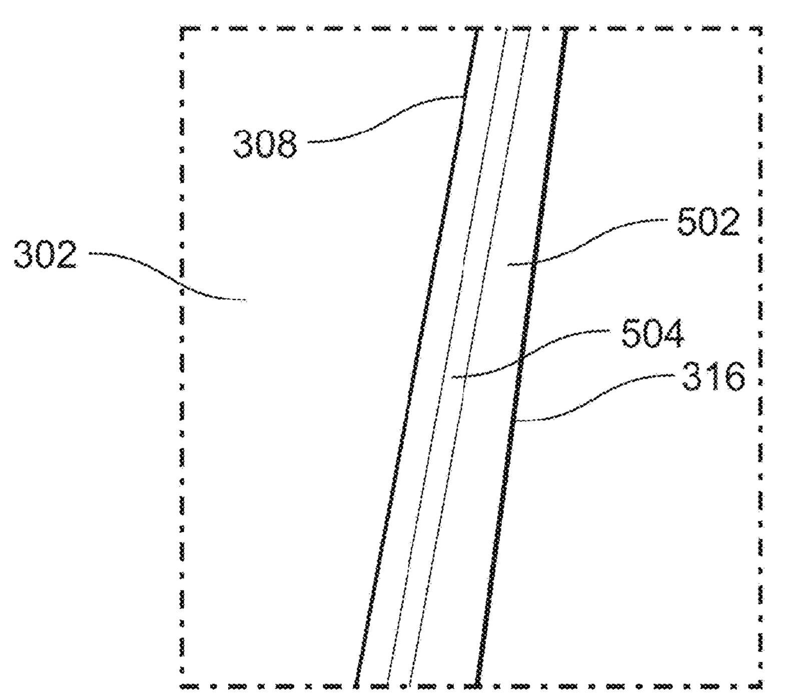
FIG. 18 is a magnified view of a portion of the candle depicted in FIG. 17.

FIGS. 17 and 18 depict yet another embodiment of a candle 500, according to another aspect of the present disclosure. Here, like the candle 400 shown in FIGS. 15 and 16, the container, jar, or vessel 306 of the candle 500 includes a first portion 502 and a second portion 504. However, in this embodiment, the second portion 504 is encapsulated by or is completely surrounded by the first portion 502 of the container 306. In this embodiment, the first portion 502 and the second portion 504 may be individually constructed from any of the aforementioned materials discussed above in connection with the container 306 of the candle 300 depicted in FIGS. For example, the first portion 502 and the second portion 504 may be individually constructed from a terracotta, clay, or ceramic material. Alternatively, or in addition, the first portion 502 and the second portion 504 may be individually constructed from a porous cement material, wood, a natural or synthetic polymer, or any of the other suitable materials previously discussed herein in connection with the container 306 of the candle 300.

In other embodiments, the vessel or container 306, as well as any portion thereof (including the interior wall 308, the exterior wall 316, the first portion 402, the second portion 404, the first portion 502, the second portion 504), may provide a visible or aesthetic impression to a user. For example, in one embodiment, the first portions 402, 502 may be a first color and the second portions 404, 504 may be a second color. According to another embodiment, the vessel or container 306, or any portion thereof, may be a first color when the vessel or container 306 is dosed or primed with the fragrance, volatile material, or active agent, and then transition to a second color once the fragrance, volatile material, or active agent emanates from or leaves the vessel or container 306. According to yet another aspect, the color or appearance of the vessel or container 306 may change or transition during use of the candles 400, 500 to provide an aesthetic effect to the candles 400, 500 (such as by providing a visually pleasing appearance or color transition) and/or a function effect to the candles 400, 500 (such as by providing a visual indication that the vessel or container 400, 500 is devoid of the fragrance, volatile material, or active agent).

In these aforementioned embodiments, the other elements of the candles 200, 300, 400, 500 can be constructed from materials known in the art. For example, the wax or fuel compositions 202, 302 of the candles 200, 300, 400, 500 can be formed from suitable hydrocarbon or wax compositions, such as soy waxes, paraffin waxes, palm waxes, a beeswax, a hydrogenated natural oil, or a combination thereof. Further, the wicks 204, 304 can be formed of any suitable material, such as cotton, linen, cellulose, plastics or ceramic material, paper, hemp, wood, metal, or any combination thereof.

In addition, for each candle 200, 300, 400, 500, the wicks 204, 304 may be a positioned a predetermined position away from the sleeve or reservoir 208 or the interior wall 210, 308 of the candles 200, 300, 400, 500. As discussed herein, unlike typical candles (such as the candle 100), the fragrance or active agent of the candles of the present disclosure is not burnt in the flame during use because the fragrance or active agent is not in the wax or fuel composition. As a result, the candles of the present disclosure emit less soot and/or VOCs as compared to a traditional candle. Therefore, in some embodiments, the wicks 204, 304 are placed a predetermined distance from the sleeve or reservoir 208 or the interior wall 210, 308 of the candles 200, 300, 400, 500 such that sleeve or reservoir 208 or the interior wall 210, 304 of the candles 200, 300, 400, 500, as well as the fragrance, volatile material, or active agent therein, are not burnt by the flame 214, 312.

Figure 19:
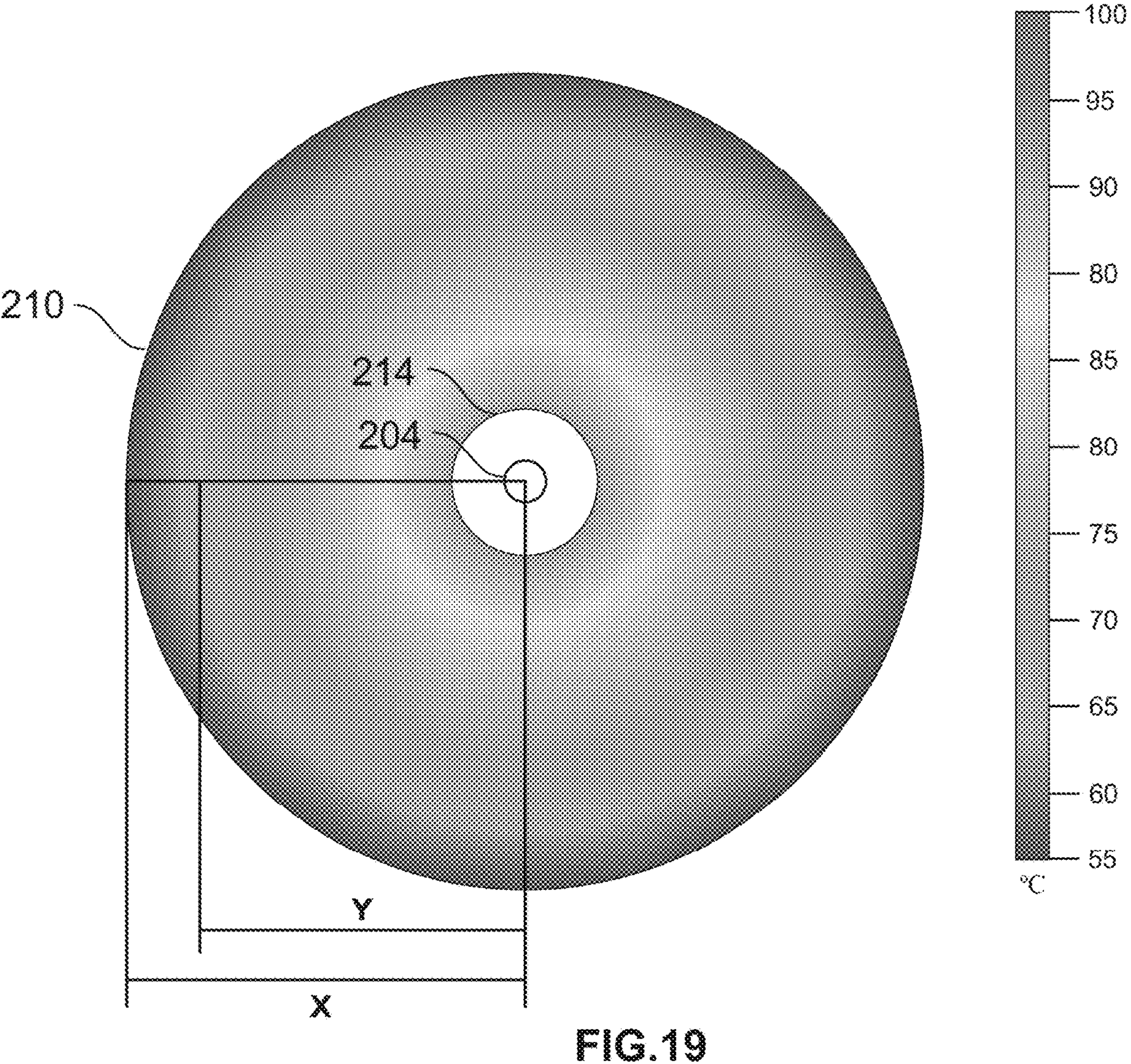
FIG. 19 is an exemplary temperature profile of the candle of FIG. 2.

More particularly, the physics of a burning candle, like the candles 200, 300, 400, 500, can be analyzed and the heat transfer and fluid flow behavior of a burning candle can be computed. For example, COMSOL Multiphysics® may be used to compute or graph a temperature profile of a flame of a candle (such as the flame 214, 312 of the candles 200, 300, 400, 500) during the life of the candle, and then an average temperature distribution produced by the candle flame can be illustrated. For example, FIG. 19 illustrates an exemplary temperature profile produced by the flame 214 of the candle 200. Here, in this example, the flame 214 of the candle 200 produces temperatures within the vessel or container 206 ranging between 55° C. and 100° C. Further, wax compositions (such as the wax or fuel compositions 202, 302) may include a melting point between 46° C. and 68° C. Therefore, the flame 214 produces temperatures sufficient to melt the wax or fuel compositions 202 positioned between the wick 204 and the interior surface 210 of the candle 200, which is a predetermined distance X away from the center of the wick 204. However, as will be further discussed, the sleeve or reservoir 208 or the interior surface 210 should be at least a distance Y away from the center of the wick 204. More particularly, the materials of the sleeve or reservoir 208, or the container or vessel 206, may have a critical temperature, at which point such material begins to burn, melt, decompose, or otherwise be consumed.

For example, some materials, such as glass, may begin to heat and exhibit undesirable effects at temperatures at or above 80° C. Additionally, the sleeve or reservoir 208 of the candle 200 may be constructed from a material that must remain below a specific temperature (e.g., 165° F. or 74° C.) to maintain its integrity. Using a computed temperature profile, such as the exemplary temperature profile illustrated in FIG. 19, the interior surface 210 and the sleeve or reservoir 208 may be positioned at least a distance Y away from the center of the wick 204, such that the integrity of the materials used to construct the interior surface and the sleeve or reservoir 208 is maintained. But to ensure that the entire wax or fuel composition 202 is exposed to enough heat to constantly melt, the interior surface 210 and the sleeve or reservoir 208 may not be positioned a predetermined distance away from the center of the wick 204 that is larger than the distance X. In one particular embodiment, for example, the distance Y may be a distance between about 30 millimeters (mm) and about 80 mm, or between about 35 mm and about 60 mm, or between about 40 mm and about 50 mm. Further, in these embodiments, the distance X may be a distance between about 35 mm and about 85 mm, or between about 45 mm and about 65 mm, or between about 45 mm and about 55 mm.

Figure 20:
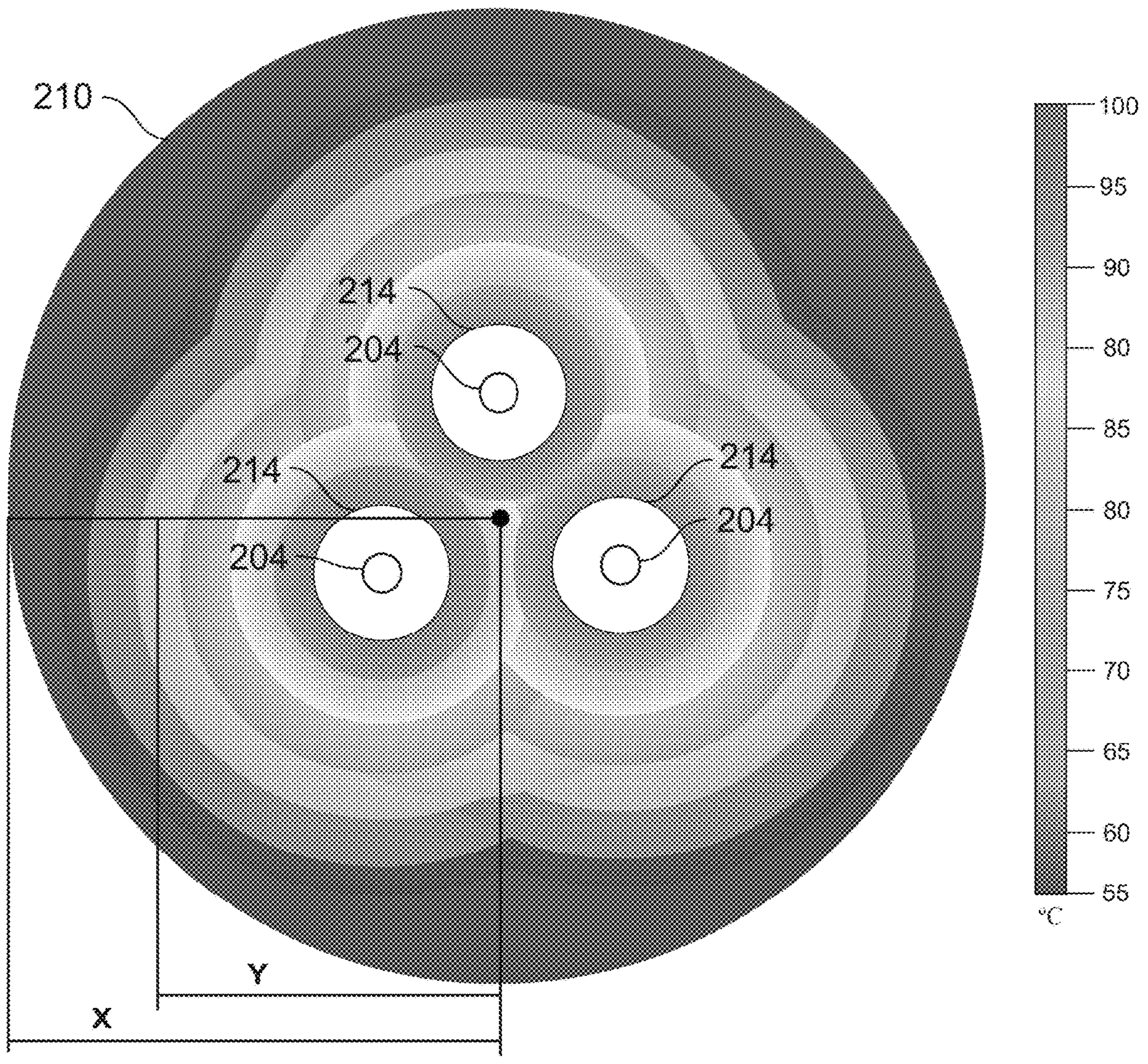
FIG. 20 is another exemplary temperature profile of another embodiment of the candle of FIG. 2.

Temperature profiles, such as the exemplary temperature profile depicted in FIG. 19, may assist in the construction of the candle, as well as the selection of the materials used for the candles 200, 300, 400, 500. The temperature profiles of a candle flame can be particularly important when selecting the materials for the vessel or container 206, the sleeve or reservoir 208 (including the individual layers 222, 224, 226), the vessel or container 306, the second portion 404, and the second portion 504. Further, although the temperature profile depicted in FIG. 19 and the discussion thereon was focused on the candle 200, it should be appreciated that the aforementioned analysis and distance determination equally applies to the candles 300, 400, 500. Even further, although the candles 200, 300, 400, 500 only include a single wick, it should be appreciated that the aspects of the present disclosure equally apply to candles having several wicks, such as two wicks, three wicks, four wicks, etc. The temperature profiles of these candles can also be computed, and the distance determination discussed above can also be performed for such candles as well. For example, FIG. 20 illustrates an exemplary temperature profile for another embodiment of the candle 200 that includes three wicks 204 and three flames 214. Here, in this embodiment, the same analysis can be conducted and the predetermined distances X, Y may be computed based on the materials used for the candle 200 and their material properties, as previously discussed herein.

In conclusion, the candles of the present disclosure include a wax or fuel composition that is essentially free of, substantially free of, or devoid of a fragrance, volatile material, or active agent. Rather than including a fragrance, volatile material, or active agent in the wax or fuel composition, the fragrance, volatile material, or active agent is in another element of the candle, such as in a sleeve or reservoir (see FIGS. 2-9) or in ajar or vessel of the candle (see FIGS. 10-18). In effect, the wax or fuel composition of the candles of the present disclosure burns and melts, which causes the exposure of the element with the fragrance, volatile material, or active agent therein. Further, the wax or fuel composition burning and melting causes continued emanation of the fragrance or volatile material from the candles of the present disclosure. Additionally, unlike typical candles (such as the candle 100), the fragrance or active agent of the candles of the present disclosure is not burnt in the flame during use because the fragrance or active agent is not in the wax or fuel composition. As a result, the candles of the present disclosure emit less soot and/or VOCs as compared to a traditional candle. Even further, as discussed herein, the candles of the present disclosure provide a more effective and improved fragrance intensity, as the fragrance will not have a smoky character from the flame of the candle, for example. Thus, the smell and delivery of the fragrance or active agent is cleaner and stronger as compared to a traditional candle of the prior art.

The candles of the present disclosure also alleviate numerous other problems of standard candles of the prior art. For example, about half of a fragrance within a conventional candle is never even experienced by a user when the conventional candle (such as the candle 100) is burned because half of the fragrance is burned as it travels up the wick into the flame of the candle. The present disclosure, however, provides a wax or fuel composition devoid, substantially free of, or essentially free of a fragrance. Because the fragrance or volatile material resides in an element of the candle removed or distinct from the wax composition, the fragrance is not at risk of being burned off during the wicking process. As such, the fragrance is not burnt in the flame of the candle and is not wasted, like standard candles of the prior art. This efficiency in emanation of the fragrance has several benefits. First, less fragrance can be used in the candles of the present disclosure without sacrificing user experience. In other words, the candles of the present disclosure can use less fragrance, yet the fragrance experienced by a user for the candles can be the same as the fragrance experience by a user for a standard candle (such as the candle 100). As a result, the candles of the present disclosure use less raw materials and can cost less than standard candles.

In addition, the candles of the present disclosure can reduce candle emissions, thereby allowing the candles of the present disclosure to pass more stringent or rigorous candle emission standards. By moving the fragrance away from the candle flame to the sleeve or reservoir or the jar or vessel, the candles of the present disclosure emit less soot and other emissions, such as VOCs, to a surrounding environment.

A further advantage of the candles of the present disclosure is the relative ease in which the candle can be manufactured with minimal impact on current production processes. As described herein, fragranced or dosed sleeves, as well as jars and vessels, can be produced on separate off-line processes that can be easily added to the manufacturing process, thereby having a minimal impact on the current production process and supply chain.

Even further, as the wax or fuel composition no longer includes a fragrance, volatile material, or active agent, the wax or fuel composition can be consistent across manufacturing lines or product lines. For example, a candle having a first fragrance may include a wax composition identical to a wax composition of a second candle having a second fragrance that is different than the first fragrance. This is advantageous for several reasons. First, the commonality and uniformity between the wax or fuel composition between products and product lines allows for the use of the same wick across products and product lines, which allows for more efficient production lines and material cost savings. Previously, for example, a first wick may be more effective at wicking a first wax composition with a first fragrance and a second wick may be more effective at wicking a second wax composition with a second fragrance; therefore, two different wicks would have to be produced or purchased and inserted into the product lines. This complexity is not present with the candles of the present disclosure because the fragrance, volatile material, or active agent is present in a portion of the candle other than the wax or fuel composition and the wax or fuel composition is devoid, essentially free of, or substantially free of a fragrance, volatile material, or active agent. Thus, a single fuel or wax composition can be used across candles or dispensers with varying fragrances, volatile materials, or active agents, and as a result, a single wick can also be used across candles or dispensers without affecting the emanation of the fragrances, volatile materials, or active agents. This also provides a more reliable candle because a candle does not need to be tested each time a new wax composition with a new fragrance is launched. Typically, several different wick sizes and materials are tested to determine the best performing wick when a new fragrance is introduced. This testing aims to ensure the wick, fragrance, and wax composition performs within a set of criteria for temperature, carbon emissions, blooms, soot emission, and curvature of the wick during use. This testing and optimization are not required for the candles of the present disclosure. Rather, an optimal wick need only be developed once and this optimal wick can be subsequently used, regardless of changes in the fragrance, volatile material, or active agent. Further, some fragrances, active agents, or volatile materials are also incompatible or insoluble with some wax or fuel compositions. As a result, some fragrances, active agents, or volatile materials cannot be used in traditional candles. The candles or dispensers of the present disclosure, however, overcome this issue because the fragrance, active agent, or volatile material is present in a portion of the candle other than the wax or fuel composition, such as a reservoir or sleeve or the container itself. The candles and dispensers of the present disclosure therefore allow the use of some fragrances, active agents, or volatile materials that were previously incompatible with traditional candles.

Additionally, although this disclosure is focused on fragranced candles, these candles and the method of producing the candles can be used for other chemical ingredients and volatile materials. For example, the embodiments of this disclosure and the method described herein could be a solution for pest control products. With that said, some fragrance material, pest control actives, and other volatile materials may be less soluble or insoluble in wax compositions. Alternatively, or additionally, some fragrances, pest control actives, and other volatile materials may suppress or inhibit a candle flame, thereby producing a less desirable flame to a user, when they are present in the wax composition. Therefore, the candles of the present disclosure are also advantageous because the placement of the fragrance or volatile material in a permeable sleeve eliminates or greatly reduces these negative effects of standard candles. More particularly, the permeable sleeve or reservoir strip can be constructed from a material that is soluble with a broader range of chemistries or can be customized to work best with various chemistries.

As discussed herein, the candle of the present disclosure produces reduced levels of soot as compared to a control candle that includes a fragrance in its wax or fuel composition. In addition, the candles of the present disclosure produce reduced levels of volatile organic compounds (VOCs) as compared to a control candle that includes a fragrance in its wax or fuel composition. In some embodiments, the reduction in emissions of soot and VOCs is at least 20%, at least 30%, at least 40%, or at least 50% compared to a control candle with the same fragrance, volatile material, or active agent in the wax composition.

The present disclosure also provides a process for producing the candles of the present disclosure. In particular, FIG. 21 schematically illustrates a method or process 600 of making the candle 200 and FIG. 22 schematically illustrates a method or process 700 of making the candles 300, 400, 500.

Figure 21:
FIG. 21 schematically illustrates a method or process of making the candles described herein.
Figure 21:
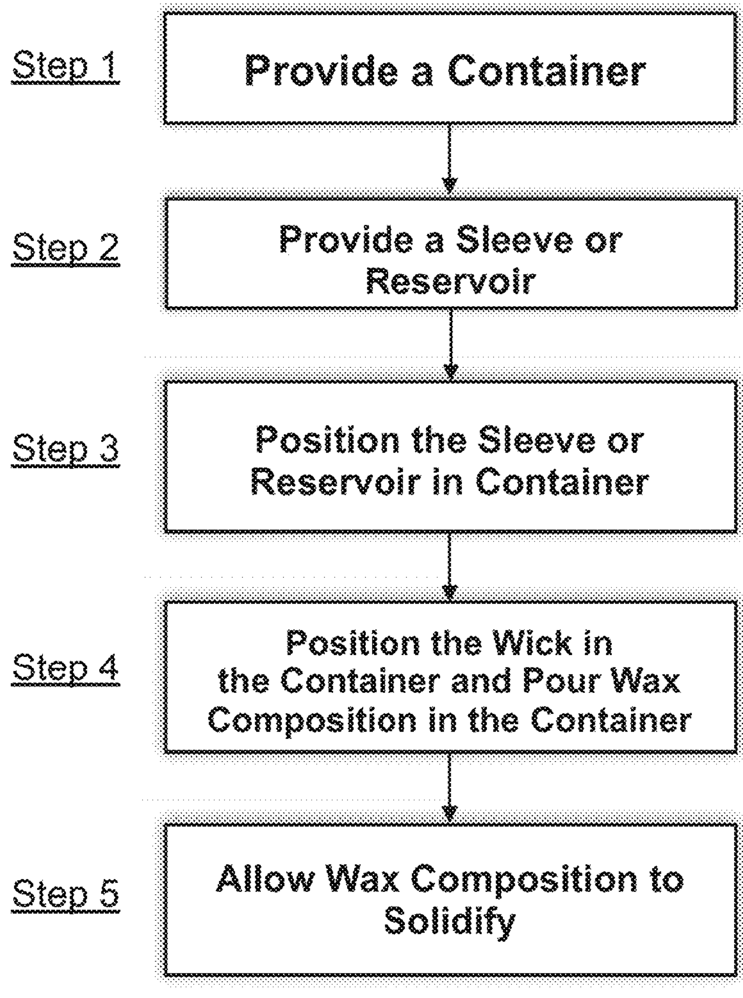

With reference to FIG. 21, Step 1 of the method 600 may include the step of providing a clean, unused jar, such as the vessel or container 206. Step 2 of the method 600 may include the step of producing or providing a sleeve or reservoir 208 dosed with a predetermined amount of fragrance, volatile material, or active agent. Alternatively, the sleeve or reservoir 208 may be essentially free of, substantially free of, or devoid of a fragrance, volatile material, or active agent. Step 3 of the method 600 may include the step of positioning the sleeve or reservoir 208 in the vessel or container 206, and adhering the sleeve or reservoir 208 to the interior wall 210 of the vessel or container 206. In the instance where the sleeve or reservoir 208 does not yet include a fragrance, volatile material, or active agent, the sleeve or reservoir 208 may be dosed with a fragrance, volatile material or active agent following Step 3 of the method 600. Regardless of when the sleeve or reservoir 208 is dosed, the method of producing the sleeve or reservoir 208 may include injection molding the sleeve or reservoir and/or the fragrance, volatile material, or active agent.

Step 4 of the method 600 may include the step of positioning the wick 204 in the vessel or container 206 and pouring the wax or fuel composition 202 into the candle vessel or container 206. Then, Step 5 of the method 600 may include the step of allowing the candle 200, which includes the container 206, the sleeve or reservoir 208, the wax or fuel composition 202, and the wick 204, to cool, such that the wax or fuel composition 202 solidifies.

Figure 22:
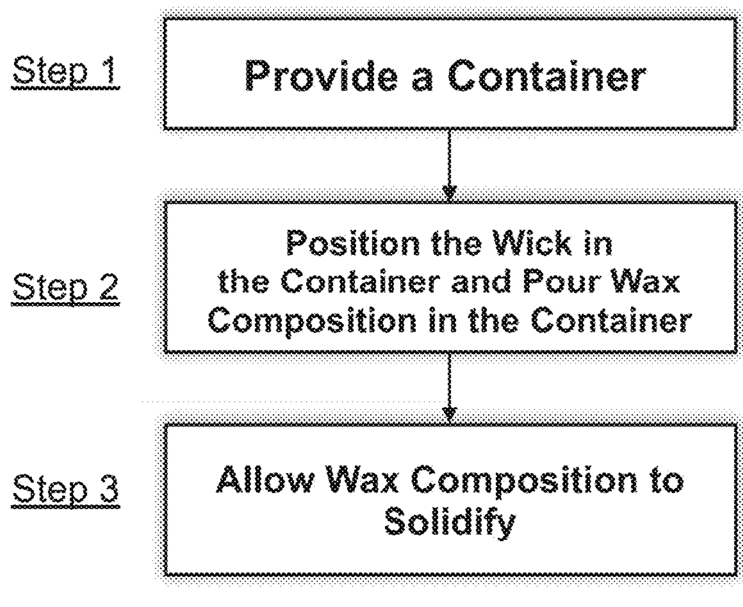
FIG. 22 schematically illustrates another method or process of making the candles described herein.

With reference to FIG. 22, Step 1 of the method 700 may include the step of producing or providing a clean, unused jar, such as the vessel or container 306. The vessel or container 306 may be dosed with a predetermined amount of fragrance, volatile material, or active agent. Alternatively, this step may include the step of introducing a liquid fragrance or volatile material to the vessel or container 306 and allowing the vessel or container 306 to absorb the liquid fragrance or volatile material. The vessel or container 306 may be produced on another manufacturing line and includes a fragrance, volatile material, or active agent therein. Then, Step 2 of the method 700 may include the step of positioning the wick 304 in the vessel or container 306 and pouring the wax or fuel composition 302 into the candle vessel or container 306. Next, Step 3 of the method 700 may include the step of allowing the candles 300, 400, 500, which include vessels or containers 306, the wax or fuel composition 302, and the wick 304, to cool, such that the wax or fuel composition 302 solidifies.

EXAMPLES

The examples herein are intended to illustrate certain embodiments of the candles and methods of producing the candles to one of ordinary skill in the art and should not be interpreted as limiting in the scope of the disclosure set forth in the claims. The candles, and the methods of making thereof, may comprise the following non-limiting examples.

Example 1

In one example, the design concept of using a fragranced plastic sleeve in lieu of fragranced wax was studied. First, two different jars having three fragranced plastic pieces (measuring 3"×½"×⅛") were placed inside a 100-millimeter (mm) diameter glass candle jar and then each jar was filled with wax. One candle (i.e., "Candle No. 1" in Table 1) had the fragranced plastic pieces (Mint) oriented lengthwise and equidistantly spaced in the jar. The second candle (i.e., "Candle No. 2" in Table 1, below) had the fragranced plastic pieces oriented horizontally and equidistantly spaced out within the jar. The wax level in both candles were at a level that covered half of the fragranced pieces. Additionally, the wax in Candle No. 1 and Candle No. 2 was non-fragranced wax and consisted of a 50/50 blend of soy and paraffin wax.

In addition to Candle No. 1 and Candle No. 2, two additional comparative candles were tested. First, a currently produced 3-wick candle having an exotic tropical blossom fragrance (i.e., "Candle No. 3" in Table 1, below) was tested in a jar having an approximate size comparable to Candle Nos. 1 and 2. Second, another currently produced 1-wick candle with an orange and neroli fragrance was tested in a jar having an approximate size comparable to Candle Nos. 1 and 2.

After formation, the candles were placed into controlled hedonic chambers and were positioned such that they would be behind a viewing screen, so as not to be observable while being evaluated. The candles were first measured in cold mode (i.e., without a flame) by evaluators who entered the chambers. During these measurements, the evaluators described the fragrance character and ranked the intensity on a scale of one to five (i.e., five being the strongest intensity). The result of this testing is shown in Table 1 below.

As shown in Table 1, the candles embodying aspects of the present disclosure (i.e., Candle No. 1 and Candle No. 2), which include the sleeves or reservoirs disclosed herein, produced increased and optimal cold modes compared to currently produced candles. These improved results were also experienced despite the fact that the exposed surfaces of the sleeves or reservoirs was limited.

TABLE 1

Results of Cold Mode Testing

| Evaluator | Measurement | Candle No. 1 | Candle No. 2 | Candle No. 3 | Candle No. 4 |
|---|---|---|---|---|---|
| 1 | Odor Description | Minty wintergreen | Gourmand sugar | Detergent clean | Eucalyptus floral |
| | Intensity | 5 | 4 | 1 | 3 |
| 2 | Odor Description | Wintergreen | None | None | Spa |
| | Intensity | 5 | 1 | 1 | 3 |

TABLE 1-continued

Results of Cold Mode Testing

| Evaluator | Measurement | Candle No. 1 | Candle No. 2 | Candle No. 3 | Candle No. 4 |
|---|---|---|---|---|---|
| 3 | Odor Description | Minty wintergreen | Gourmand sugar | None | Floral |
| | Intensity | 3 | 3 | 1 | 3 |
| 4 | Odor Description | Fresh air | Gourmand van | Gourmand | Fresh air |
| | Intensity | 2 | 2 | 1 | 1 |
| 5 | Odor Description | Nutmeg | Sweet and warm | None | Spicy |
| | Intensity | 2.5 | 2 | 1 | 2 |
| | Average | 3.9 | 2.5 | 1.0 | 2.8 |

Example 2

Next, the same candles from Example 1 were tested in a hot mode (i.e., with a lighted flame). Here, the candles were lit and compared in a hot mode using the same method, and the same criteria of intensity and fragrance character as used in Example 1. The result of these measurements are shown in Table 2, below.

As shown in Table 2, a significant jump in fragrance intensity was observed when the candles were lit, even when exposed surface area was limited. In particular, the candles employing aspects of the present disclosure produced fragrance intensities that either matched or exceeded those of currently produced candles. Further, Candle No. 1 and Candle No. 2 produced high intensities when lit, which caused the fragrances to fill the room much more quickly compared to comparative Candle No. 3 and Candle No. 4. Thus, these results showcase the beneficial aspects of candles of the present disclosure.

TABLE NO. 2

Results of Hot Mode Testing

| Evaluator | Measurement | Candle No. 1 | Candle No. 2 | Candle No. 3 | Candle No. 4 |
|---|---|---|---|---|---|
| 1 | Odor Description | Mint | Vanilla | Tropical | Floral |
| | Intensity | 5 | 4 | 5 | 4 |
| 2 | Odor Description | Gourmand | Gourmand | Tropical Blossom | Loral, eucalyptus |
| | Intensity | 5 | 4.5 | 5 | 3.5 |
| 3 | Odor Description | Spearmint | Hawaiian Breeze | Tropical floral, fruity | Herbal citrus |
| | Intensity | 5 | 5 | 2 | 3 |
| 4 | Odor Description | Wintergreen | Vanilla | Vanilla Sweet Gourmand | Floral |
| | Intensity | 5 | 3 | 3 | 3 |
| 5 | Odor Description | Wintergreen | Vanilla | Tropical | Light white flower |
| | Intensity | 4.5 | 4 | 5 | 2 |
| 6 | Odor Description | Wintergreen | Lily | "Do not like!" | Orange |
| | Intensity | 3 | 4 | 5 | 3 |
| 7 | Odor Description | Mint green | Vanilla Cookie | Tropical floral, fruity | Coastal Citrus |
| | Intensity | 4.5 | 4 | 4 | 3 |
| 8 | Odor Description | Wintergreen | Hawaiian Breeze type but plasticky | Tropical blossoms | Orange and naroli |
| | Intensity | 5 | 4.5 | 4 | 2.5 |
| 9 | Odor Description | Mint | Fruity | Fruity | Fruity |
| | Intensity | 4.5 | 4.5 | 4 | 4.5 |
| | Average | 4.6 | 4.3 | 4.3 | 3.1 |

Example 3

The hedonics of candles of the present disclosure were further tested and compared to standard and currently produced candles. In this example, the embodiments of the present disclosure utilizing fragranced porous jars in lieu of fragranced wax was studied again. Here, several candles were made in small terracotta pots having 3" openings at the top. Further, an exterior of the pot of the candles was coated with a Rustoleum spray enamel and approximately 150 grams of wax was used to produce each candle. Additionally, two candles (i.e., “Candle No. 1” and “Candle No. 3” in Table 3, below) were produced as standard or comparable candles having 8 grams (g) of fragrance added to 150 g of wax. Alternatively, two candles employing aspects of the present disclosure (i.e., “Candle No. 2” and “Candle No. 4” in Table 3, below) were produced by soaking the porous jars in 8 g of fragrance and then loading 150 g of non-fragranced wax to the interior of the jars. After solidification of the wax, holes were drilled into the wax and wicks were added. Further, one of the comparative candles (i.e., Candle No. 3) and one of the candles employing aspects of the present disclosure (i.e., Candle No. 4) were burned half-way down to expose roughly half of the interior surface of their respective jars. Additionally, each of the four candles were tested in fragrance chambers and evaluators rated the intensity and differences between the four candles using the same methods discussed above in connection with Examples 1 and 2. The results of this testing are shown in Table 3 below.

As shown in Table 3, the candles of the present disclosure had comparable or improved intensities compared to comparative candles. Further, as the interior surface of the jar became exposed, the intensity of the fragrance of Candle No. 4, which employed aspects of the present disclosure, greatly exceeded that of the comparative candles (i.e., Candle No. 1 and Candle No. 3). Additionally, Candle No. 2 still had some cold throw and fragrance intensity, but the fragrance was also better preserved in the interior of the jar (as evidenced by the lower intensity prior to being lit and burnt), thereby allowing more fragrance to be observed by a user during use, which is a beneficial aspect of candles of the present disclosure. As such, these results showcase the improved fragrance intensity resulting from aspects of the present disclosure.

TABLE 3

| Hedonics Testing Results | | | | | | | |
|---|---|---|---|---|---|---|---|
| Candle No. 1 | Candle No. 2 | Candle No. 3 | Candle No. 4 | Overall | Candle No. 1 vs. Candle No. 2 | Candle No. 3 vs. Candle No. 4 | Comments |
| 3 | 3 | 3 | 3 | 5 | Very different | slightly different | 2, 3, and 4 are similar. 1 is more woody/pine. |
| 2 | 2 | 2 | 3 | 3 | Very different | very different | Too weak overall. Room 4 is best-would probably like more if stronger |
| 3 | 2 | 2 | 4 | 4 | slightly different | slightly different | #4 was strongest for me so I liked it best. |
| 3 | 2 | 3 | 4 | 2 | slightly different | slightly different | |
| 4 | 5 | 4 | 4 | 4 | slightly different | very different | Very waxy fatty notes in room #3 |
| 2 | 1 | 2 | 1 | 4 | Very different | slightly different | Less is definitely more. I liked where I could get a hint and barely smell it |
| 3 | 2 | 4 | 5 | 4 | Very different | slightly different | Room 2 was very weak compared to the others. Room 4 smelled best. |
| 3 | 1 | 5 | 4 | 4 | Very different | slightly different | Fragrance 3 was awful fragrance 4 was the best fragrance 2 was hardly noticeable |
| 2.9 | 2.3 | 3.1 | 3.5 | 3.8 | Very different | slightly different | 2, 3, and 4 are similar. 1 is more woody/pine. |

Example 4

The weight loss and cold mode intensity of candles of the present disclosure were further tested. In one example, the cold mold intensity and weight loss of a standard candle and a candle employing aspects of the present disclosure were tested. More particularly, Candle No. 1 shown in Table 4 below was a standard candle that included 150 grams of wax, about 9 grams of which was fragrance, and Candle No. 2 was a candle soaked in a fragrance to include about 4.50 grams of fragrance. For Candle No. 2, 150 grams of wax was loaded into the interior of the jar. Additionally, in this example, the weight and intensity of the fragrance was tested over a 46-day period and at specific days along such period. Further, for this particular example, the intensity of the fragrance was tested on a scale of one (i.e., lowest intensity) to ten (i.e., highest intensity). The result of this testing is shown in Table 4 below.

As shown in Table 4, the candle embodying aspects of the present disclosure provided better cold mode intensity than standard or comparable candles for about 13 days. Further, the candle embodying aspects of the present disclosure provided consistent cold mode intensity for the full 46-day testing period and nearly comparable cold mode intensity to standard or comparable candles presently produced.

TABLE 4

Weight Loss and Cold Mode Intensity

| | Weight (g) | | Cold Mode Intensity | | Weight Loss (g) | |
|---|---|---|---|---|---|---|
| Days | Candle No. 1 | Candle No. 2 | Candle No. 1 | Candle No. 2 | Candle No. 1 | Candle No. 2 |
| 0 | 313.68 | 321.42 | 7 | 10 | 0.00 | 0.00 |
| 4 | 313.66 | 321.23 | 6 | 9 | 0.02 | 0.19 |
| 7 | 313.63 | 321.10 | 6 | 9 | 0.05 | 0.32 |
| 10 | 313.66 | 320.99 | 6 | 8 | 0.02 | 0.43 |
| 13 | 313.66 | 320.89 | 7 | 7 | 0.02 | 0.53 |
| 17 | 313.53 | 320.73 | 7 | 6 | 0.15 | 0.69 |
| 19 | 313.62 | 320.72 | 7 | 6 | 0.06 | 0.70 |
| 25 | 313.56 | 320.60 | 7 | 6 | 0.12 | 0.82 |
| 31 | 313.53 | 320.51 | 7 | 5 | 0.15 | 0.91 |
| 46 | 313.50 | 320.30 | 6 | 5 | 0.18 | 1.12 |

Example 5

The benzene emissions of several candles were also tested. In this example, several standard candles (i.e., "Candle No. 1", "Candle No. 2", and "Candle No. 3" in Table 5, below) were constructed using 75 grams of wax, about 4.5 grams of which was fragrance. Further, several candles embodying aspects of the present disclosure (i.e., "Candle No. 4", "Candle No. 5", "Candle No. 6", "Candle No. 7", "Candle No. 8", and "Candle No. 9" in Table 5, below) were constructed by soaking jars in fragrance to allow the jars to absorb the fragrance therein. In particular, Candle Nos. 4-6 included approximately 4.5 grams of fragrance therein and Candle Nos. 7-9 included approximately 2.25 grams of fragrance therein. Further, Candle Nos. 4-9 were also filled with about 75 grams of non-fragranced wax. Additionally, each candle was burned for approximately 30 minutes before being tested according to EM-001 emission collection methods. The candle emission results are shown in Table 5 below.

As shown in Table 5, the highest levels of benzene emissions occurred in Candle Nos. 1-3, which were the standard or comparable candles. Candle Nos. 4-9, which employed aspects of the present disclosure demonstrated significantly lower benzene or VOC emissions compared to Candle Nos. 1-3, thereby showcasing the improved aspects (i.e., lower VOC emissions) resulting from the candles of the present disclosure.

| Sample | Sample | ng benzene on GC tube | Average |
|---|---|---|---|
| Candle No. 1 | 1 | 12.99 | 11.85 |
| Candle No. 2 | 2 | 8.35 | |
| Candle No. 3 | 3 | 14.21 | |
| Candle No. 4 | 1 | 3.29 | 4.47 |
| Candle No. 5 | 2 | 3.76 | |
| Candle No. 6 | 3 | 6.37 | |
| Candle No. 7 | 1 | 3.33 | 2.75 |
| Candle No. 8 | 2 | 1.90 | |
| Candle No. 9 | 3 | 3.01 | |

Variations and modifications of the foregoing are within the scope of the present disclosure. It is understood that the embodiments disclosed and defined herein extend to all alternative combinations of two or more of the individual features mentioned or evident from the text and/or drawings. All of these different combinations constitute various alternative aspects of the present disclosure. The embodiments described herein will enable others skilled in the art to utilize the disclosure. The claims are to be construed to include alternative embodiments to the extent permitted by the prior art.

As noted previously, it will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

INDUSTRIAL APPLICABILITY

The aspects of the candle and process of making same described herein advantageously create a candle having improved emissions and manufacturing.

Numerous modifications to the present invention will be apparent to those skilled in the art in view of the foregoing description. Accordingly, this description is to be construed as illustrative only and is presented for the purpose of enabling those skilled in the art to make and use the invention. The exclusive rights to all modifications which come within the scope of the appended claims are reserved.

The invention claimed is:

1. A volatile material dispensing device, comprising:
a container,
a wax composition,
a wick, and
a sleeve having a volatile material,
wherein the sleeve is positioned between the wax composition and the container.

2. The volatile material dispensing device of claim 1, wherein the wax composition is essentially free of a fragrance.

3. The volatile material dispensing device of claim 1, wherein the sleeve is constructed from a permeable material capable of passive emanation of the volatile material.

4. The volatile material dispensing device of claim 1, wherein the wax composition and the container enclose the sleeve and the volatile material.

5. The volatile material dispensing device of claim 4, wherein the volatile material dispensing device further comprises a strip having the volatile material, and the strip is positioned above the wax composition.

6. The volatile material dispensing device of claim 1, wherein a portion of the sleeve extends above the wax composition and is exposed.

7. The volatile material dispensing device of claim 1, wherein the volatile material is selected from the group consisting of a fragrance or a pest control agent.

8. The volatile material dispensing device of claim 1, wherein the volatile material dispensing device is a candle.

9. The volatile material dispensing device of claim 1, wherein the volatile material dispensing device includes three wicks.

10. The volatile material dispensing device of claim 9, wherein the sleeve is positioned at least partially between the wax and the container, and the sleeve includes three reservoirs positioned radially outward from the wicks.

11. The volatile material dispensing device of claim 1, wherein the sleeve is constructed from a material selected from the group consisting of a polyethylene (PE), a polyvinyl alcohol (PVOH), a polypropylene (PP), an ethylene-vinyl acetate (EVA), a high-density polyethylene (HDPE), an ethylene vinyl alcohol (EVOH), or a blend thereof.

12. A volatile material dispensing device, comprising:

a container having a permeable interior surface, a non-permeable exterior surface, and a volatile material within the container;

a wax composition; and a wick.

13. The volatile material dispensing device of claim 12, wherein the wax composition is essentially free of a fragrance.

14. The volatile material dispensing device of claim 12, wherein the non-permeable exterior wall includes a sealant layer.

15. The volatile material dispensing device of claim 12, wherein the volatile material is selected from the group consisting of a fragrance or a pest control agent.

16. The volatile material dispensing device of claim 12, wherein the volatile material dispensing device is a candle.

17. The volatile material dispensing device of claim 12, wherein a portion of the permeable interior surface of the container is exposed.

18. The volatile material dispensing device of claim 12, wherein the container is constructed from a material comprising at least one of terracotta and concrete.

19. The volatile material dispensing device of claim 16, wherein the candle includes three wicks.

20. A method of making a candle, the method including the steps of:

providing a container and a reservoir having a volatile material, wherein the reservoir comprises polyethylene (PE), a polyvinyl alcohol (PVOH), a polypropylene (PP), an ethylene-vinyl acetate (EVA), a high-density polyethylene (HDPE), an ethylene vinyl alcohol (EVOH), or a blend thereof;

positioning the reservoir adjacent an interior surface of the container;

positioning a wick in the container;

pouring a wax composition in the container; and allowing the wax composition to solidify.

* * * * *